United States Patent
Terliuc

(10) Patent No.: US 8,529,440 B2
(45) Date of Patent: Sep. 10, 2013

(54) ENDOSCOPY SYSTEMS

(75) Inventor: Gad Terliuc, Ra'anana (IL)

(73) Assignee: SMART Medical Systems Ltd., Raanana (IL)

( * ) Notice: Subject to any disclaimer, the term of this patent is extended or adjusted under 35 U.S.C. 154(b) by 925 days.

(21) Appl. No.: 12/307,271

(22) PCT Filed: Jul. 4, 2007

(86) PCT No.: PCT/IL2007/000832
§ 371 (c)(1),
(2), (4) Date: Jan. 1, 2009

(87) PCT Pub. No.: WO2008/004228
PCT Pub. Date: Jan. 10, 2008

(65) Prior Publication Data
US 2009/0287058 A1    Nov. 19, 2009

Related U.S. Application Data

(60) Provisional application No. 60/818,505, filed on Jul. 6, 2006.

(51) Int. Cl.
*A61B 1/06* (2006.01)
*A61B 1/00* (2006.01)
*A61B 1/04* (2006.01)

(52) U.S. Cl.
USPC ............ 600/172; 600/104; 600/112; 600/127

(58) Field of Classification Search
USPC ................ 600/104, 106, 112, 114, 121–125, 600/127, 129, 160, 172, 175
See application file for complete search history.

(56) References Cited

U.S. PATENT DOCUMENTS

| 4,040,413 A | 8/1977 | Ohshiro |
| 4,066,070 A | 1/1978 | Utsugi |
| 4,148,307 A | 4/1979 | Utsugi |
| 4,176,662 A | 12/1979 | Frazer |
| 4,195,633 A | 4/1980 | Nehring et al. |
| 4,195,637 A | 4/1980 | Gruntzig et al. |
| 4,224,929 A | 9/1980 | Furihata |
| 4,445,892 A | 5/1984 | Hussein et al. |
| 4,453,545 A | 6/1984 | Inoue |
| 4,616,652 A | 10/1986 | Simpson |

(Continued)

FOREIGN PATENT DOCUMENTS

| WO | WO 83/01893 | 6/1983 |
| WO | WO 99/53827 | 10/1999 |

(Continued)

OTHER PUBLICATIONS

An Office Action dated Sep. 28, 2009, which issued during the prosecution of Applicant's Australian Patent Application No. 2005211257.

(Continued)

*Primary Examiner* — Alireza Nia
(74) *Attorney, Agent, or Firm* — Daniel J. Swirsky; AlphaPatent Associates Ltd.

(57) ABSTRACT

An endoscope insertion assembly for performing endoscopy, including an endoscope insertion tube operative for passage through a body cavity, and an optical assembly operative for inspection of the body cavity, the optical assembly being selectably insertable within the endoscope insertion tube.

10 Claims, 46 Drawing Sheets

(56) References Cited

U.S. PATENT DOCUMENTS

| | | | |
|---|---|---|---|
| 4,646,722 | A | 3/1987 | Silverstein et al. |
| 4,646,988 | A | 3/1987 | Campbell |
| 4,676,228 | A | 6/1987 | Krasner et al. |
| 4,807,593 | A | 2/1989 | Ito |
| 4,862,874 | A | 9/1989 | Kellner |
| 4,983,165 | A | 1/1991 | Loiterman |
| 5,025,778 | A | 6/1991 | Silverstein et al. |
| 5,050,585 | A | 9/1991 | Takahashi |
| 5,135,001 | A | 8/1992 | Sinofsky et al. |
| 5,259,366 | A | 11/1993 | Reydel et al. |
| 5,518,501 | A | 5/1996 | Oneda et al. |
| 5,577,992 | A | 11/1996 | Chiba et al. |
| 5,653,677 | A * | 8/1997 | Okada et al. .................. 600/112 |
| 5,662,587 | A | 9/1997 | Grundfest et al. |
| 5,679,110 | A | 10/1997 | Hamazaki |
| 5,685,853 | A * | 11/1997 | Bonnet .................... 604/164.01 |
| 5,711,756 | A * | 1/1998 | Chikama ...................... 600/112 |
| 5,762,604 | A | 6/1998 | Kieturakis |
| 5,876,329 | A | 3/1999 | Harhen |
| 5,879,287 | A * | 3/1999 | Yoshihashi .................. 600/160 |
| 5,938,586 | A | 8/1999 | Wilk et al. |
| 5,961,445 | A * | 10/1999 | Chikama ...................... 600/112 |
| 6,007,482 | A | 12/1999 | Madni et al. |
| 6,161,049 | A | 12/2000 | Rudie et al. |
| 6,162,171 | A | 12/2000 | Ng et al. |
| 6,309,346 | B1 | 10/2001 | Farhadi |
| 6,461,294 | B1 | 10/2002 | Oneda et al. |
| 6,485,409 | B1 | 11/2002 | Voloshin et al. |
| 6,585,639 | B1 | 7/2003 | Kotmel et al. |
| 6,663,589 | B1 | 12/2003 | Halevy |
| 6,689,056 | B1 * | 2/2004 | Kilcoyne et al. ............. 600/300 |
| 6,702,735 | B2 | 3/2004 | Kelly |
| 6,951,554 | B2 | 10/2005 | Johansen et al. |
| 7,056,284 | B2 | 6/2006 | Martone et al. |
| 7,169,105 | B2 | 1/2007 | Iwasaka et al. |
| 7,442,166 | B2 * | 10/2008 | Huang et al. .................. 600/160 |
| 2002/0143237 | A1 | 10/2002 | Oneda et al. |
| 2002/0156347 | A1 | 10/2002 | Kim et al. |
| 2004/0102681 | A1 | 5/2004 | Gross |
| 2005/0038335 | A1 | 2/2005 | Gross et al. |
| 2005/0059931 | A1 | 3/2005 | Garrison et al. |
| 2005/0124856 | A1 | 6/2005 | Fujikura et al. |
| 2005/0125005 | A1 | 6/2005 | Fujikura |
| 2005/0133453 | A1 | 6/2005 | Woodruff et al. |
| 2005/0137457 | A1 | 6/2005 | Machida |
| 2005/0159645 | A1 | 7/2005 | Bertolero et al. |
| 2005/0165233 | A1 | 7/2005 | Hamedi et al. |
| 2005/0165273 | A1 | 7/2005 | Takano |
| 2005/0256373 | A1 * | 11/2005 | Bar-Or et al. ................. 600/114 |
| 2005/0273021 | A1 | 12/2005 | Burgermeister |
| 2006/0111610 | A1 | 5/2006 | Machida |
| 2006/0111611 | A1 * | 5/2006 | Eizenfeld et al. ............ 600/124 |
| 2006/0161044 | A1 | 7/2006 | Oneda et al. |
| 2006/0241345 | A1 | 10/2006 | Oishi et al. |
| 2007/0244361 | A1 | 10/2007 | Ikeda et al. |

FOREIGN PATENT DOCUMENTS

| | | |
|---|---|---|
| WO | WO 02/064028 | 10/2001 |
| WO | WO 03/080155 | 3/2003 |
| WO | WO 2004/101059 | 11/2004 |

OTHER PUBLICATIONS

An Office Action dated Oct. 9, 2009, which issued during the prosecution of Applicant's U.S. Appl. No. 10/588,131.

An Office Action dated Apr. 9, 2010, which issued during the prosecution of Applicant's U.S. Appl. No. 10/588,131.

An Office Action dated Nov. 3, 2007, which issued during the prosecution of Applicant's Chinese Patent Application No. 200580004311.4.

An Office Action dated Jan. 25, 2010, which issued during the prosecution of Applicant's Chinese Patent Application No. 200810173921.2.

An International Search Report dated Sep. 1, 2005, which issued during the prosecution of Applicant's PCT/IL05/00152.

An International Search Report dated Jun. 2, 2010, which issued during the prosecution of Applicant's PCT/IL09/00940.

An International Search Report dated Sep. 1, 2009, which issued during the prosecution of Applicant's PCT/IL09/00322.

An International Search Report dated Jul. 9, 2009, which issued during the prosecution of Applicant's PCT/IL08/00687.

An International Search Report dated Jul. 18, 2008, which issued during the prosecution of Applicant's PCT/IL07/00832.

An International Search Report dated Apr. 21, 2008, which issued during the prosecution of Applicant's PCT/IL05/00849.

An International Search Report dated May 19, 2008, which issued during the prosecution of Applicant's PCT/IL07/00600.

Sleeve Expander Tool product, manufactured by HellermannTyton of 7930 N. Faulkner Road., Milwaukee, Wisconsin USA, and commercially distributed in the UK by Canford Audio PLC of Crowther Road, Washington, UK under catalog No. 55-601.

Double Balloon Endoscope product, including EN-450T5 enteroscope, TS-13140 overtube and BS-2 front balloon, which interface with balloon pump control BP-20 and 2200 video system, all commercially available from Fujinon Inc., of 10 High Point Drive, Wayne, New Jersey, USA.

Single Balloon Endoscope product, including SIF-Q 180 enteroscope, ST- SB1 overtube, which interface with balloon pump control OBCU and EVIS EXERA II system video system, all commercially available from Olympus Inc., of 3500 Corporate Parkway Center Valley, PA 18034-0610, USA.

An Office Action dated Mar. 23, 2009, which issued during the prosecution of Applicant's Israel Patent Application No. 177148. (Including a translation of the relevant part).

An English Abstract of JP 2003-250896, Sep. 2003.

An Office Action dated Sep. 23, 2009, which issued during the prosecution of Applicant's Israel Patent Application No. 177148. (Including a translation of the relevant part).

* cited by examiner

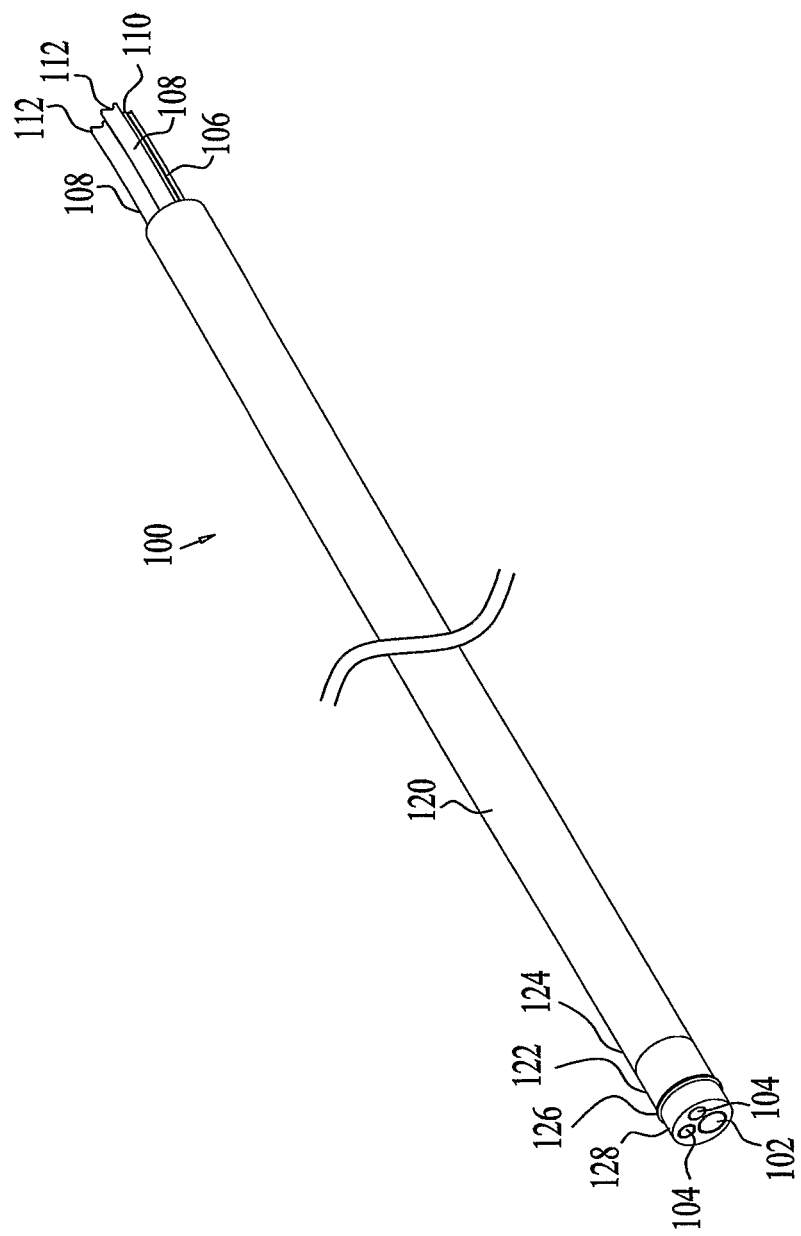

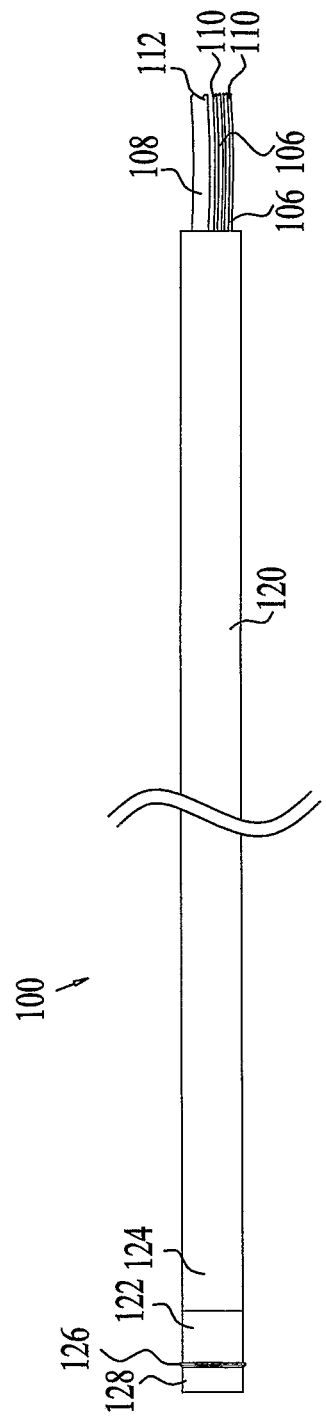
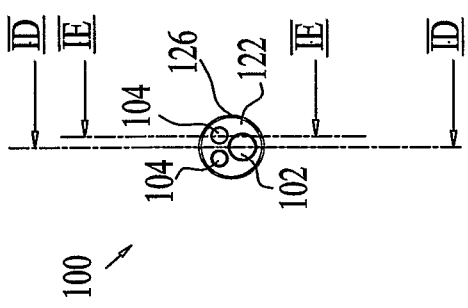

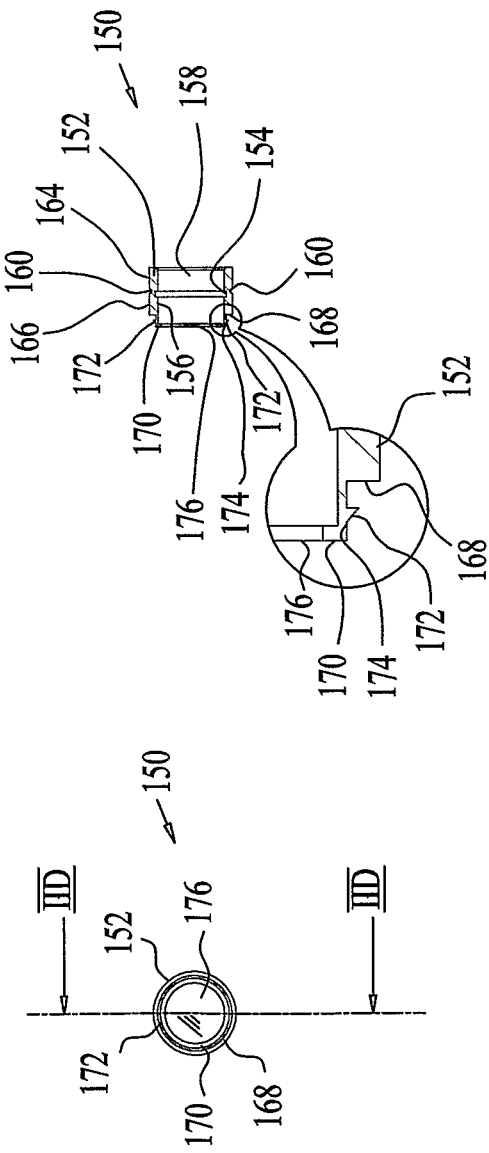

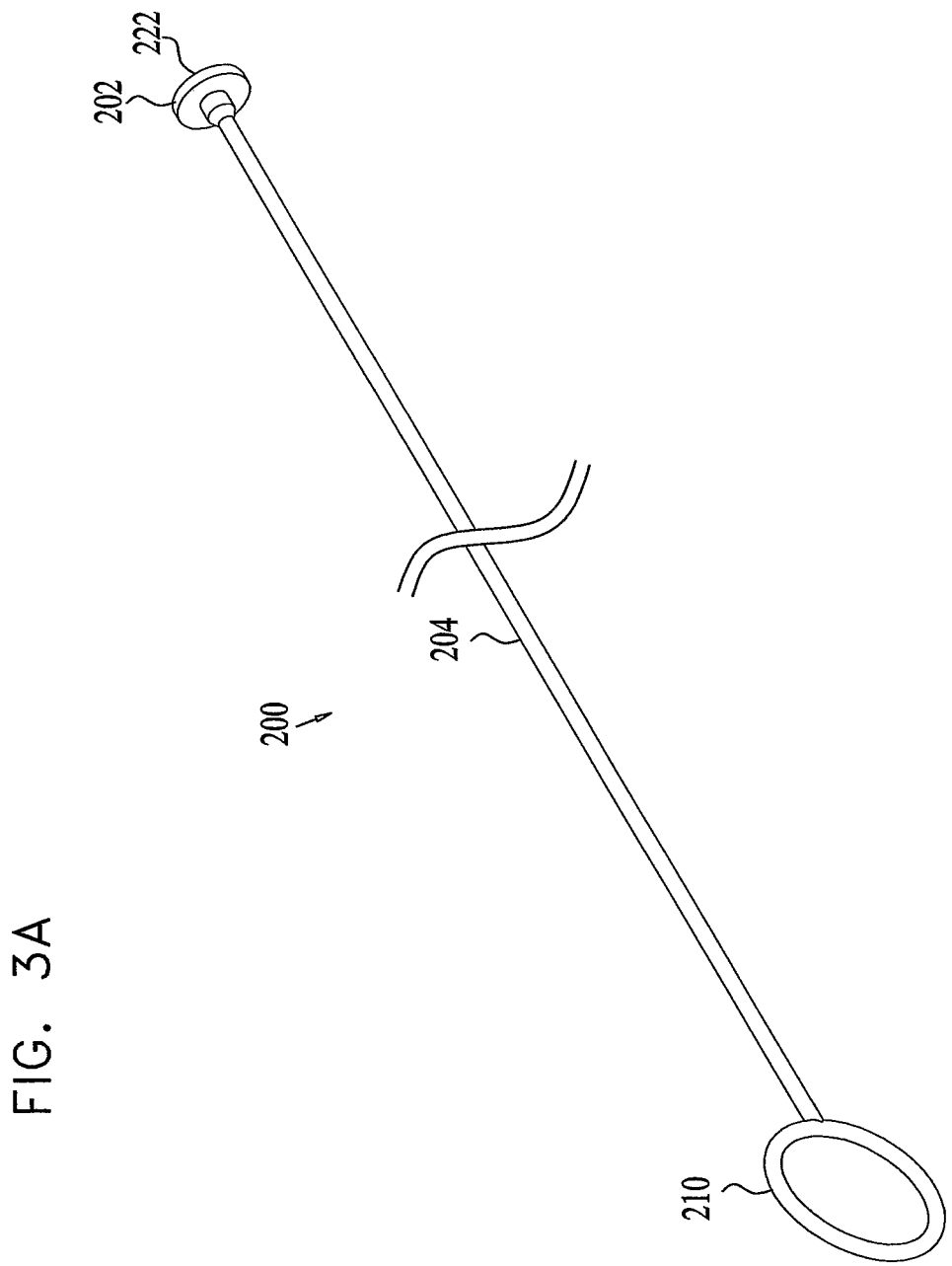

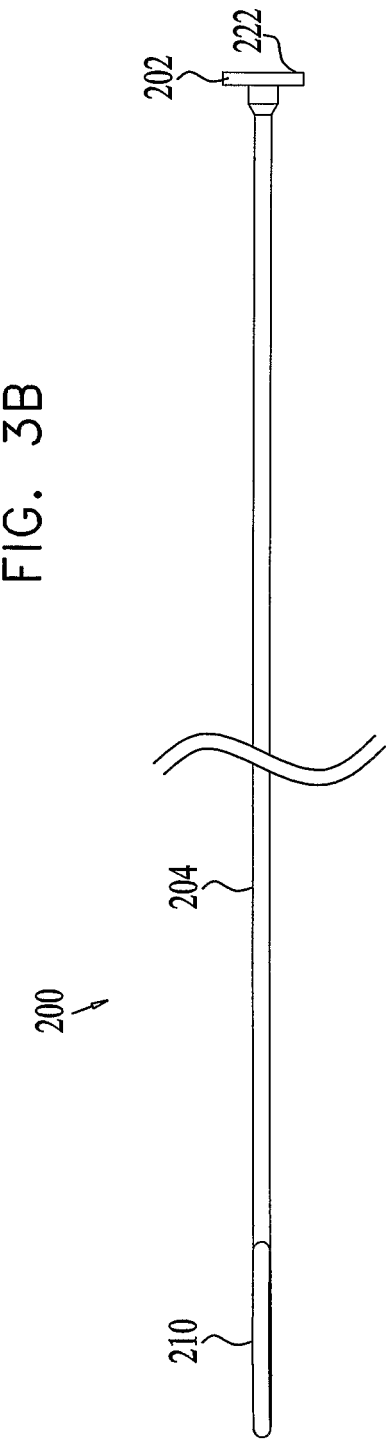
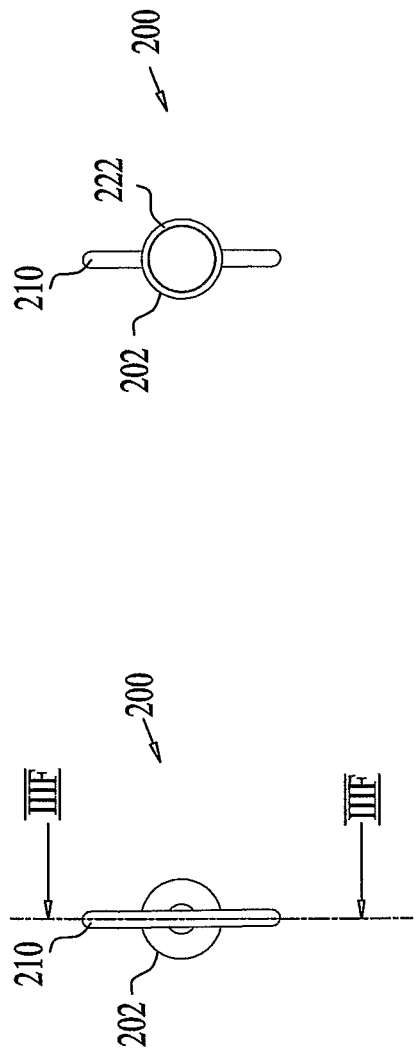
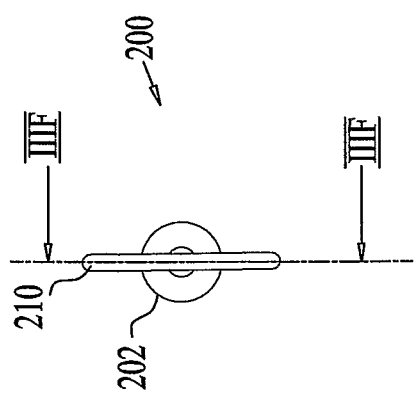
FIG. 3B
FIG. 3D
FIG. 3C

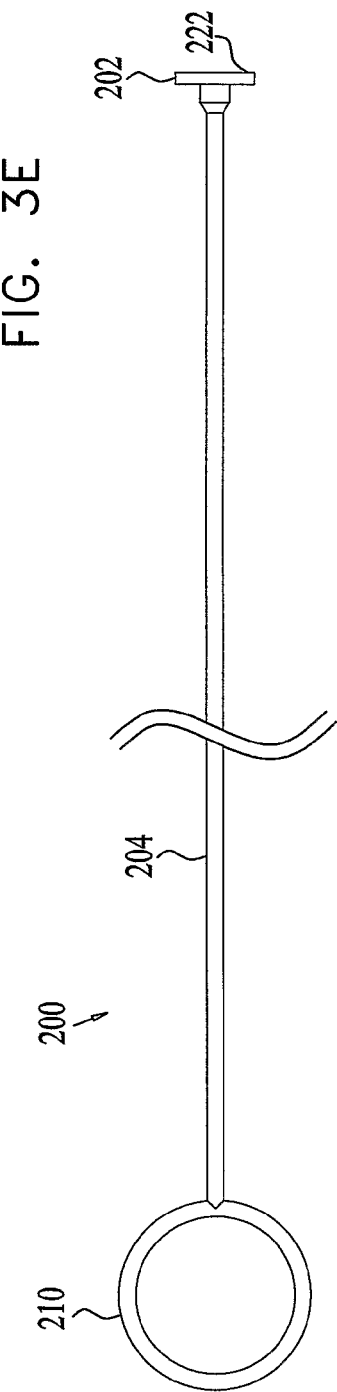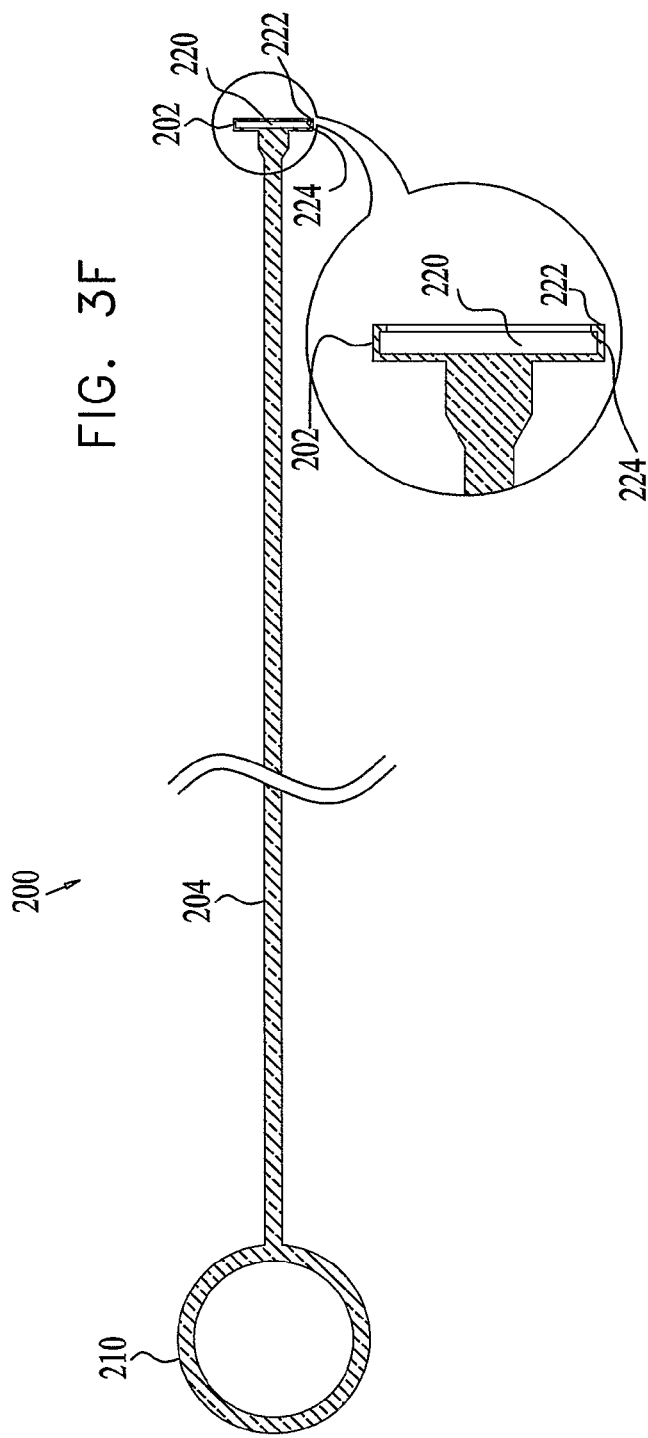

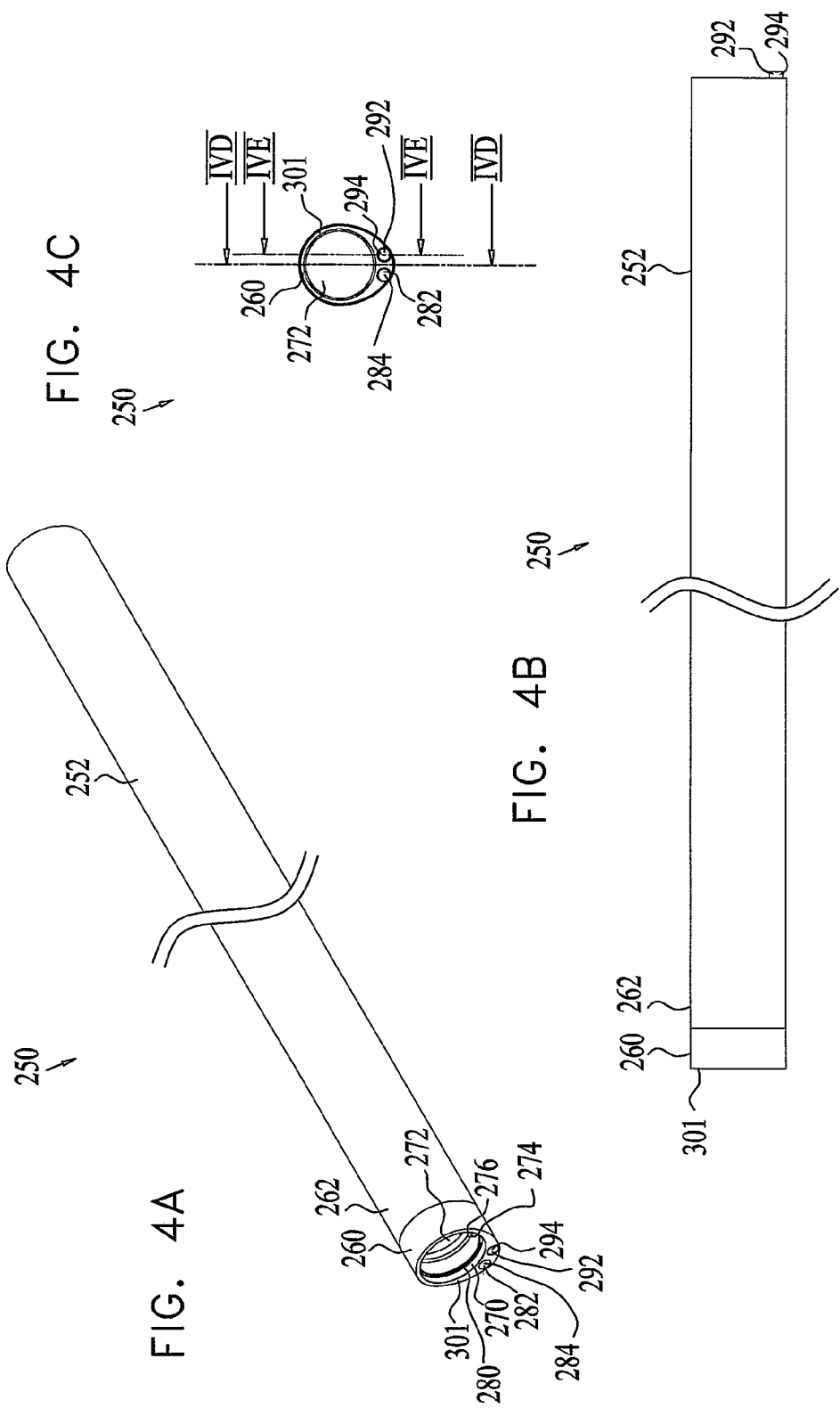

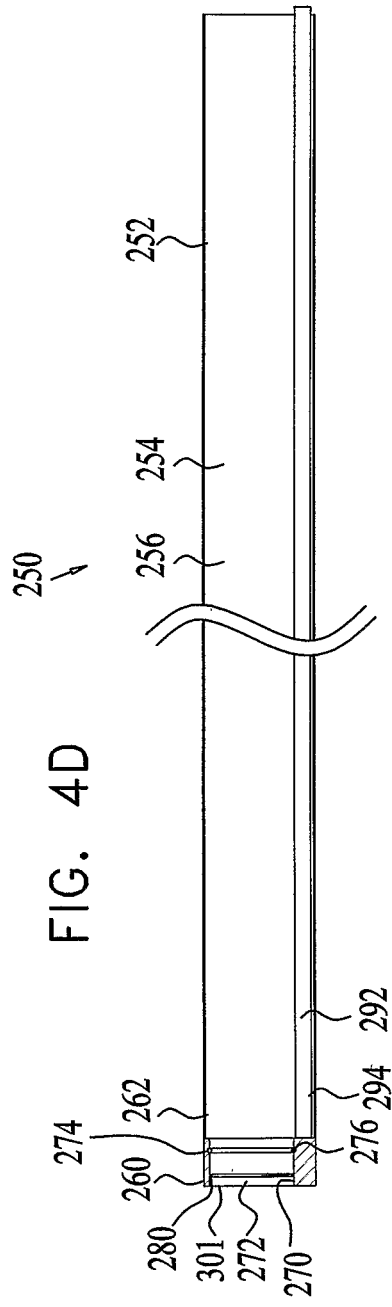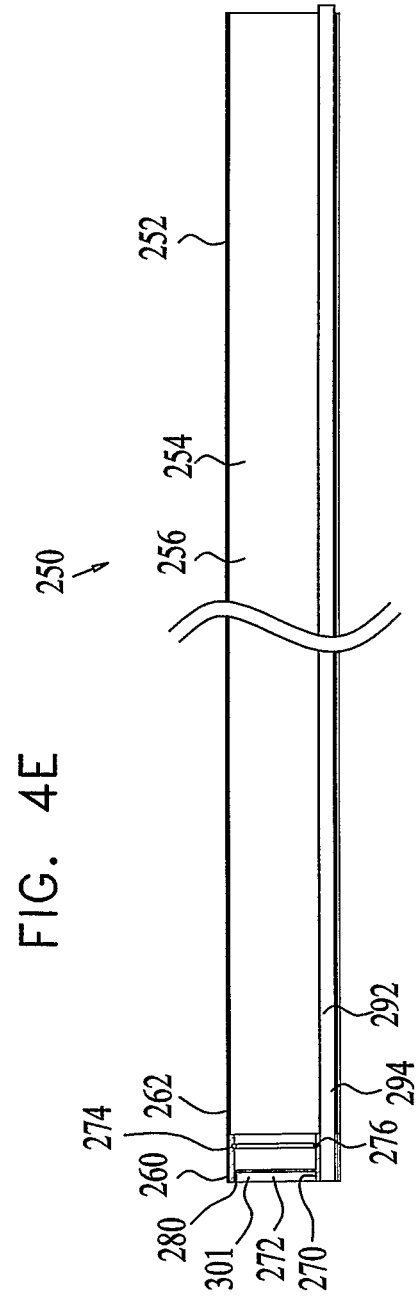

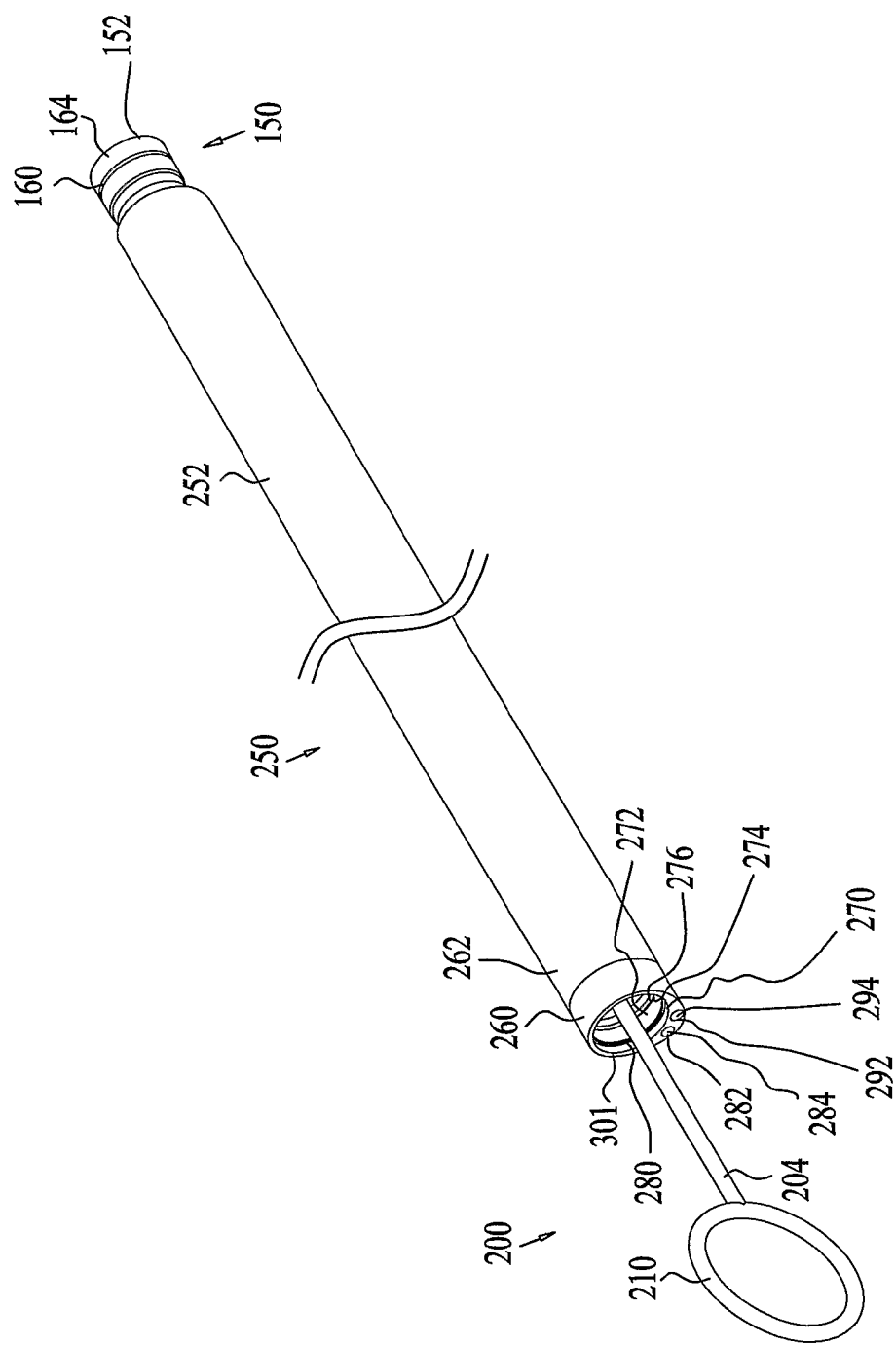

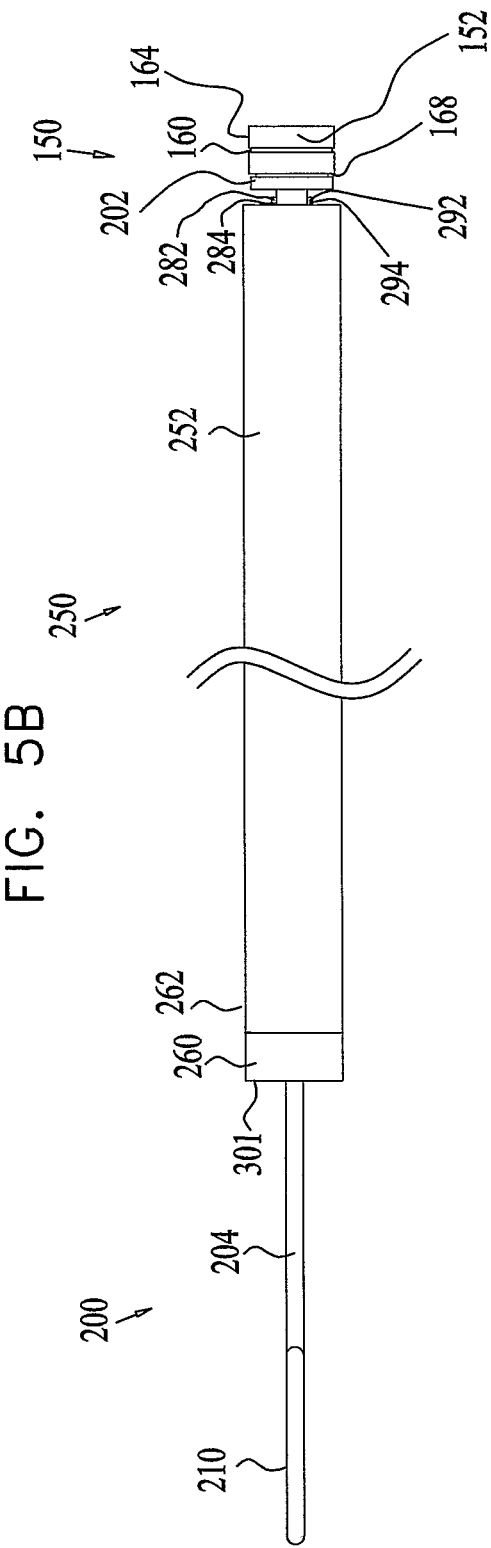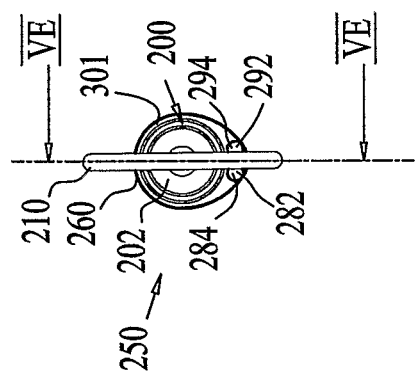
FIG. 5B
FIG. 5C

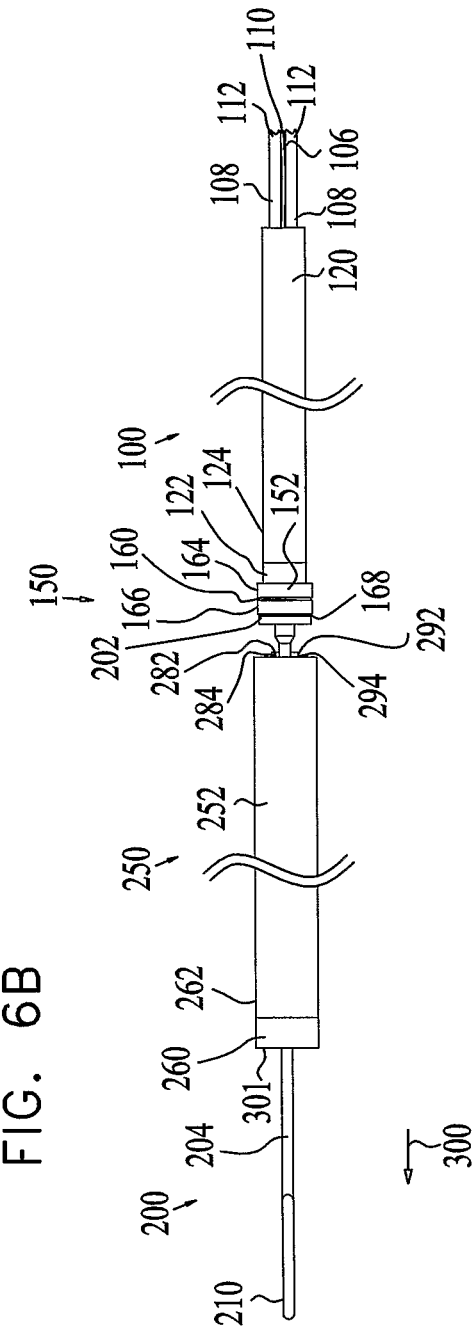
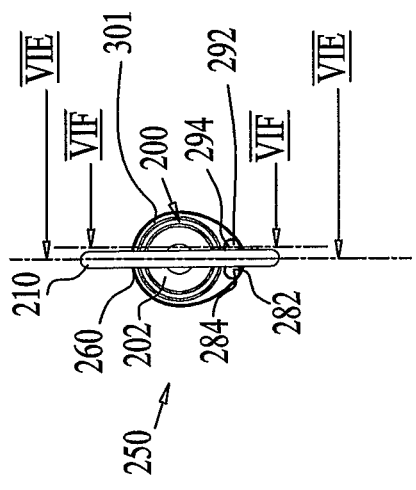
FIG. 6B
FIG. 6C

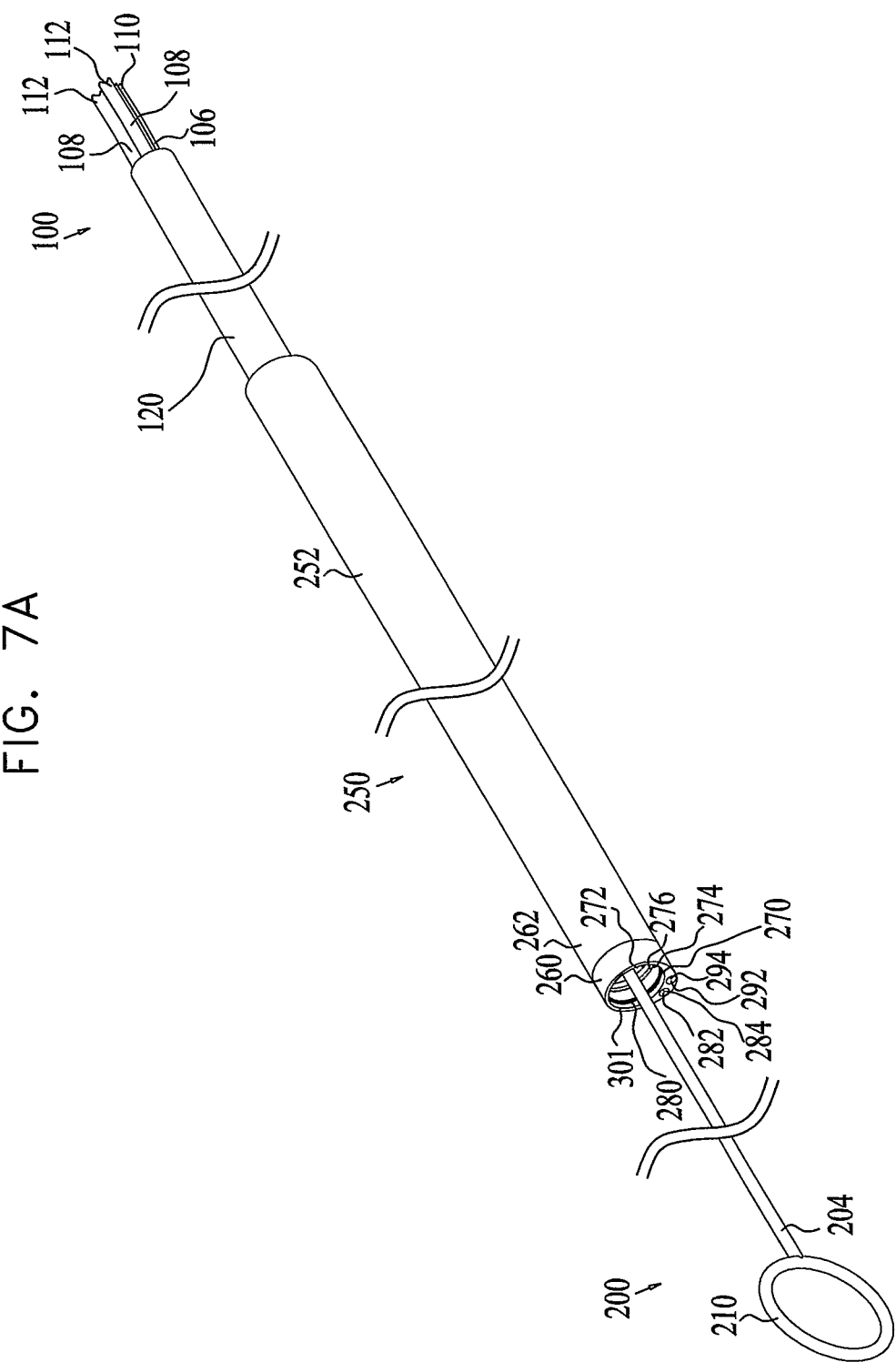

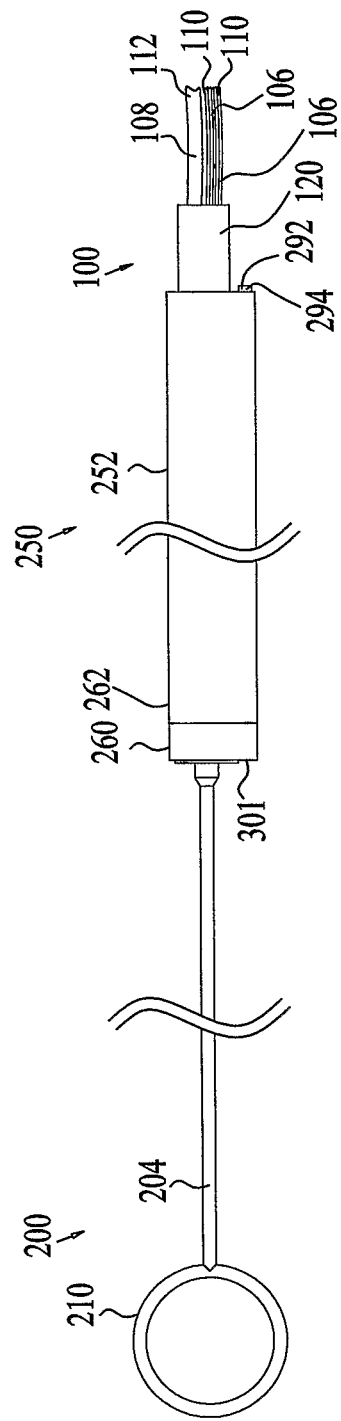

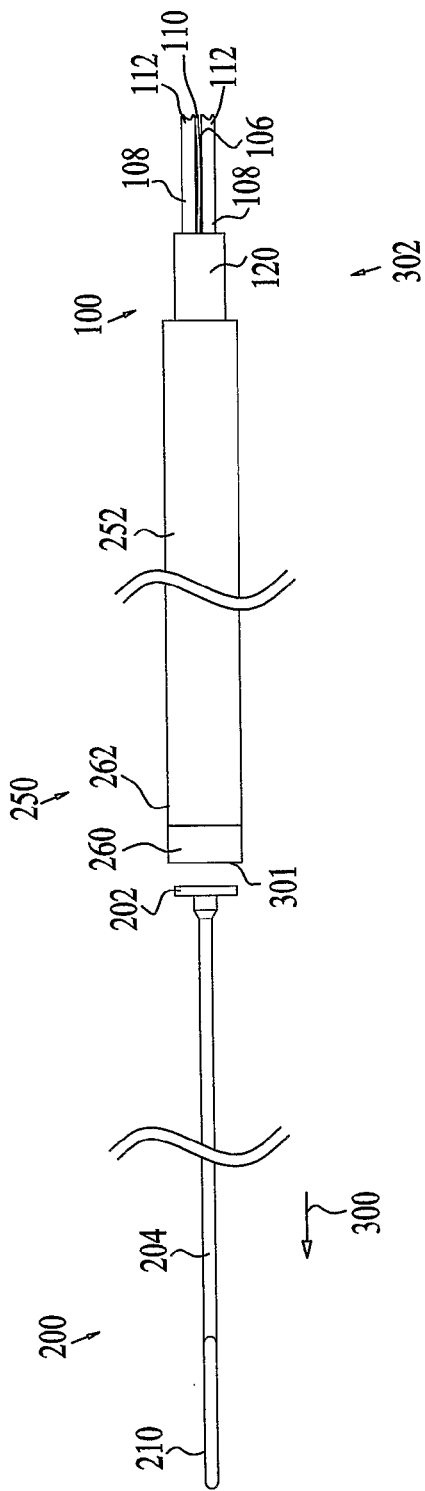
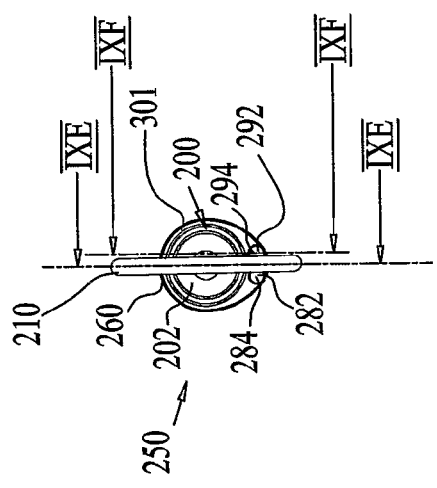
FIG. 9B
FIG. 9C

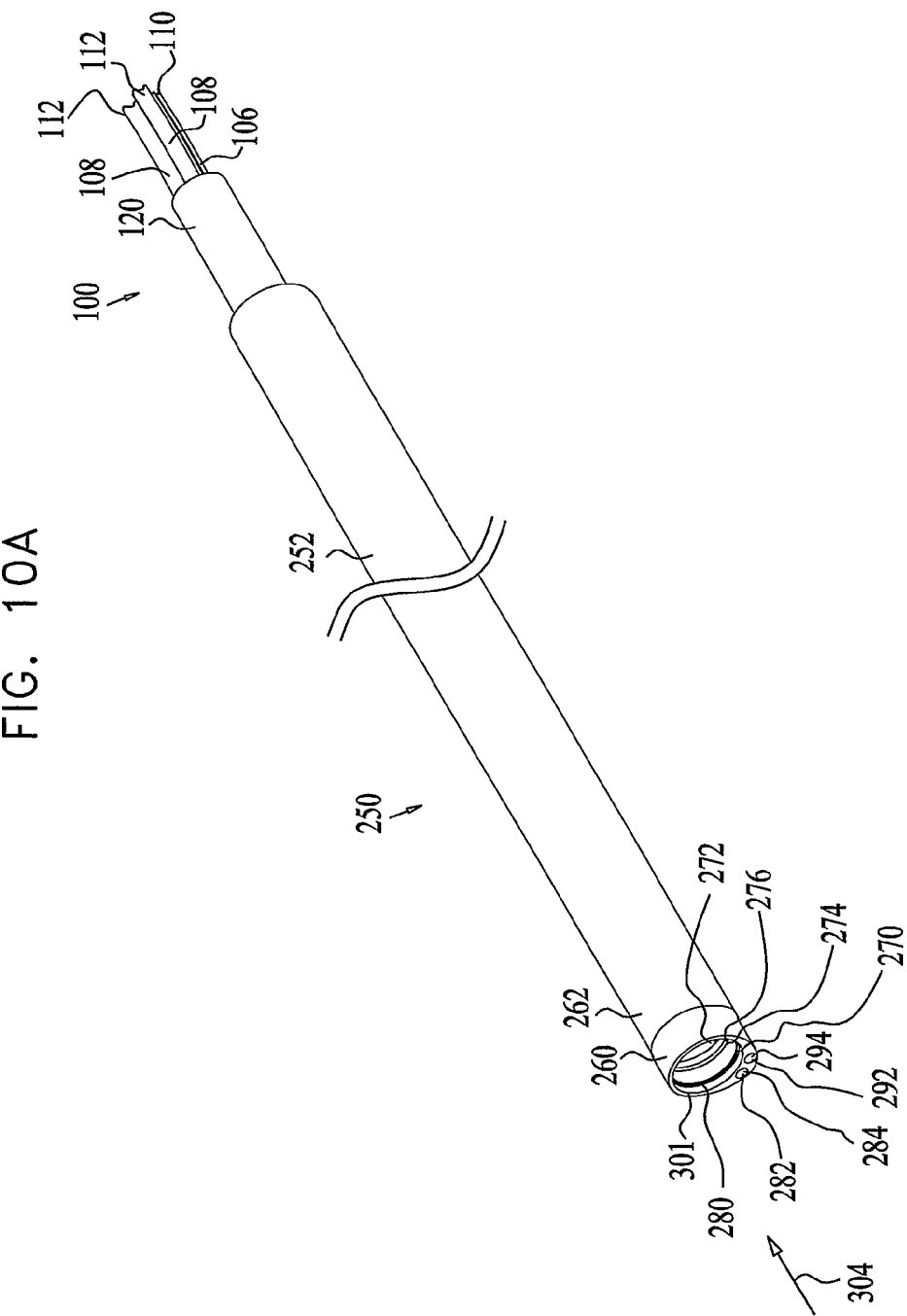

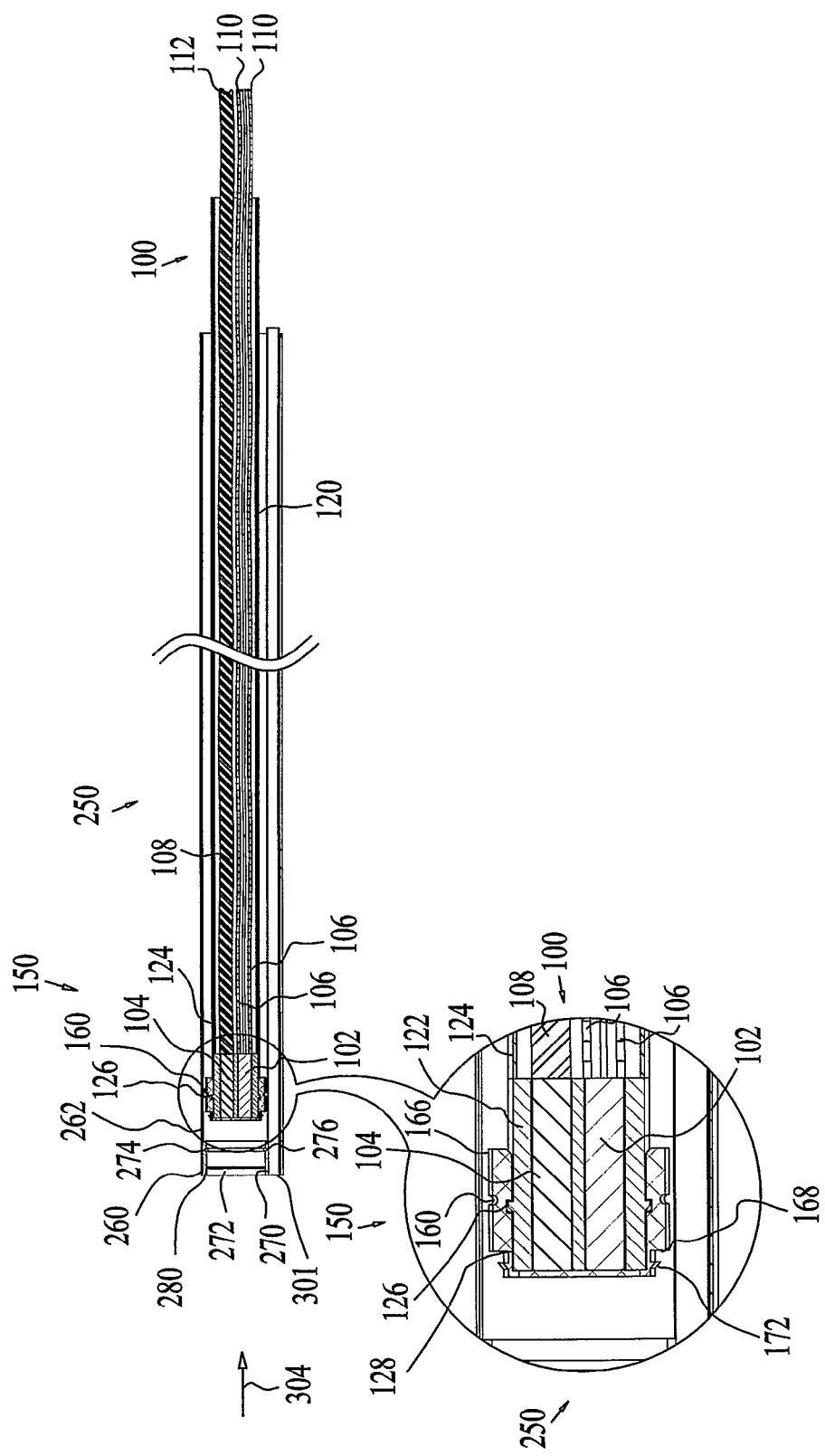

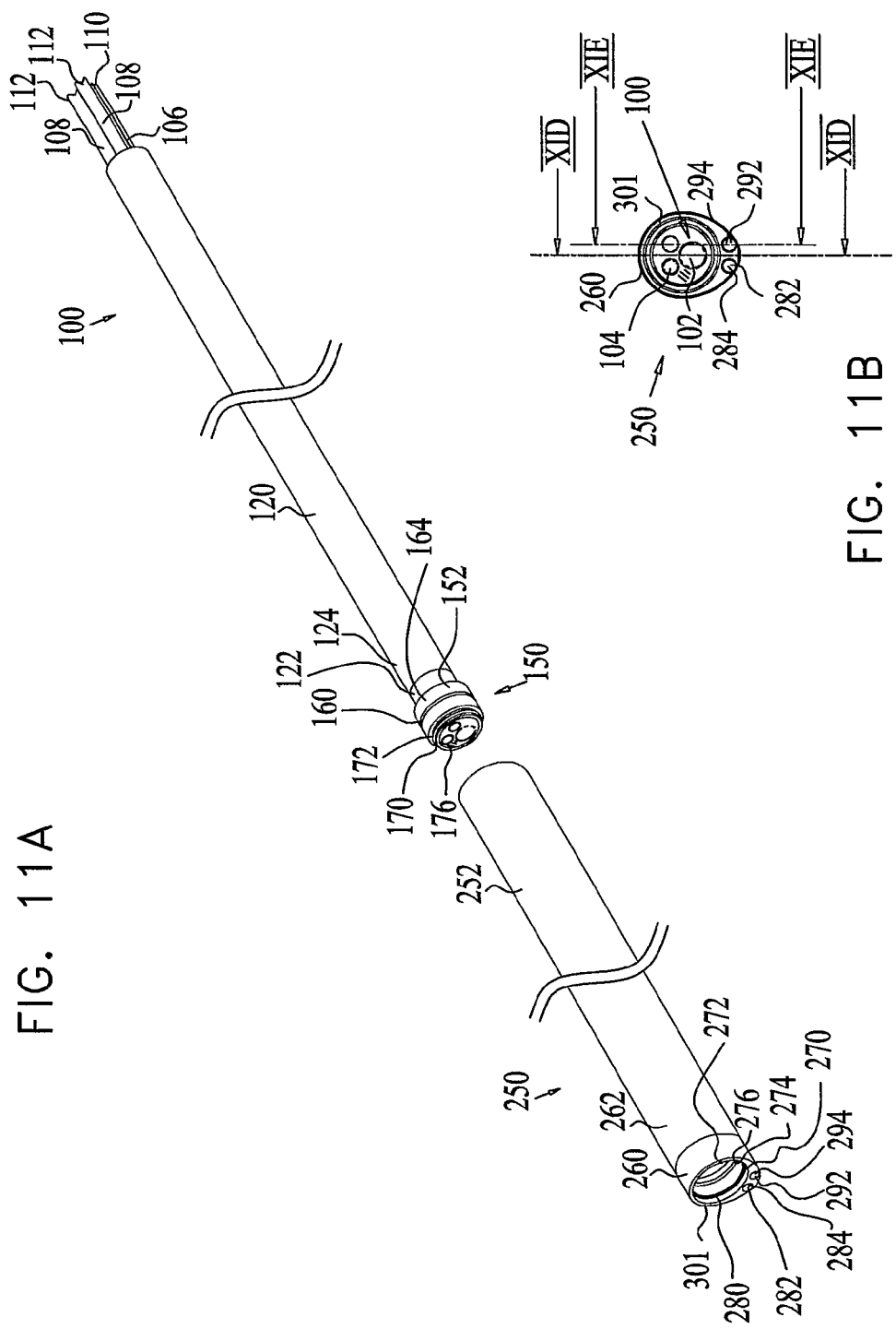

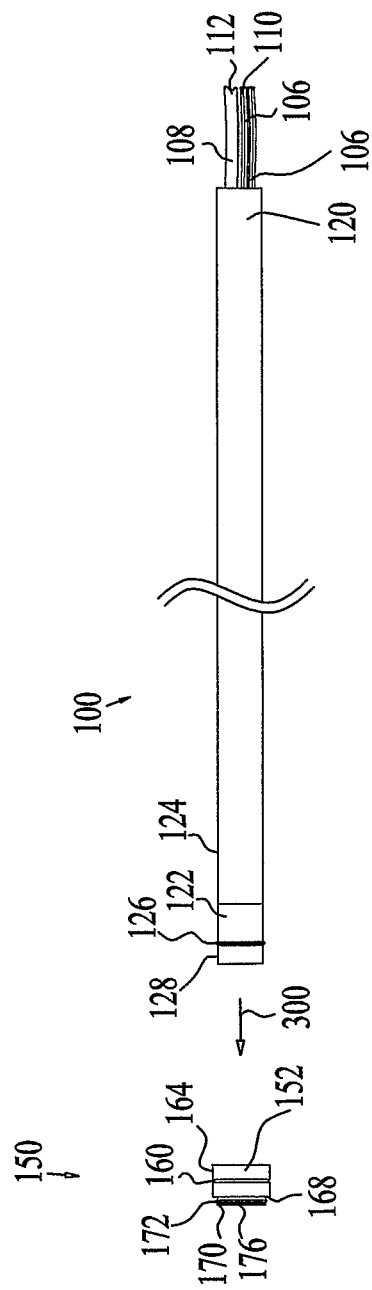

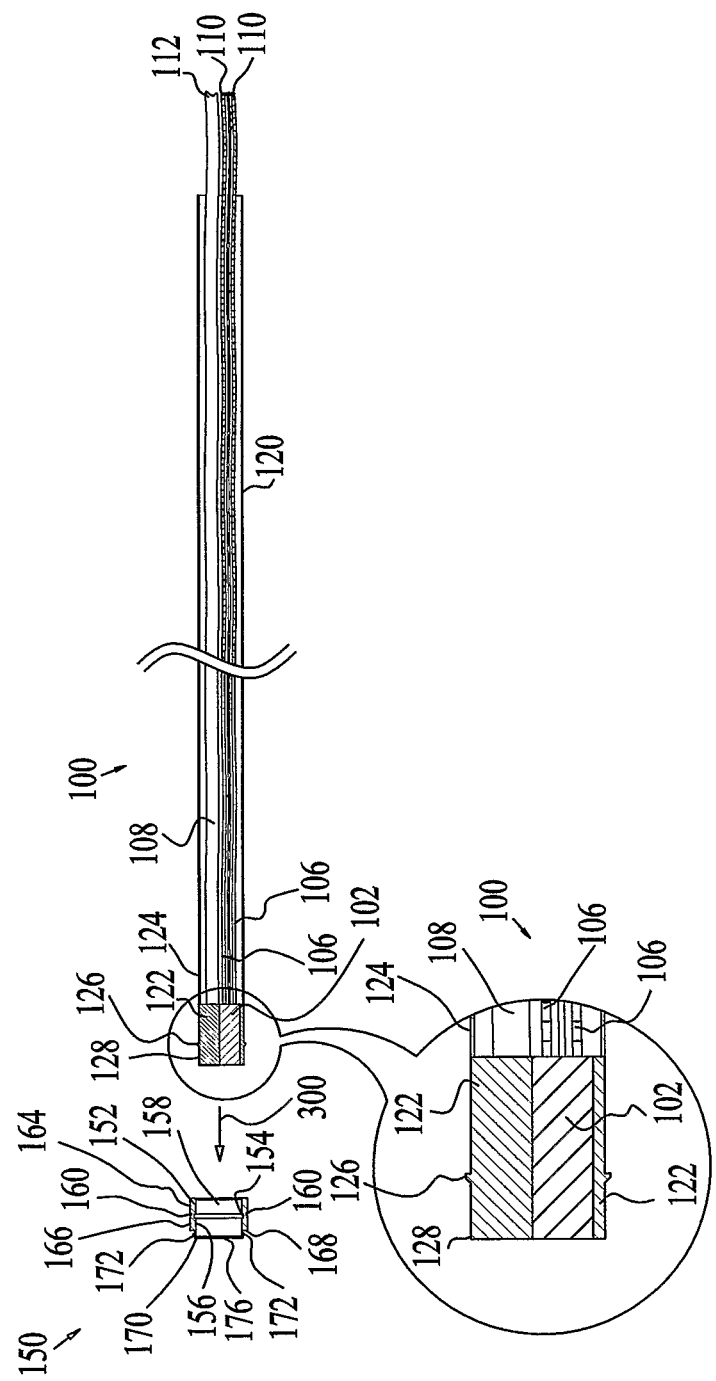

ENDOSCOPY SYSTEMS

REFERENCE TO RELATED APPLICATIONS

This application is a U.S. National Phase Application under 35 U.S.C. 371 of PCT International Application No. PCT/IL2007/000832, which has an international filing date of Jul. 4, 2007, and which claims priority from U.S. Provisional Patent Application No. 60/818,505, filed Jul. 6, 2006, the disclosures of which are incorporated herein by reference in their entirety.

Reference is made to applicant's copending PCT Application No. PCT/IL2005/000152, filed Feb. 7, 2005, and PCT Application No. PCT/IL2005/000849, filed Aug. 8, 2005, the disclosures of which are hereby incorporated by reference.

FIELD OF THE INVENTION

The present invention relates generally to endoscope systems.

BACKGROUND OF THE INVENTION

The following patent publications are believed to represent the current state of the art:

U.S. Pat. Nos. 5,518,501; 5,876,329; and 6,485,409.

SUMMARY OF THE INVENTION

There is thus provided in accordance with a preferred embodiment of the present invention an endoscope insertion assembly for performing endoscopy, including an endoscope insertion tube operative for passage through a body cavity, and an optical assembly operative for inspection of the body cavity, the optical assembly being selectably insertable within the endoscope insertion tube.

In accordance with a preferred embodiment of the present invention the optical assembly is selectably detachable from the endoscope insertion tube. Preferably, the endoscope insertion assembly includes a coupling element operative for engaging the optical assembly with the endoscope insertion tube. Additionally, the endoscope insertion tube and the coupling element are operative to isolate the optical assembly from fluids external to the endoscope insertion assembly.

In accordance with another preferred embodiment of the present invention the coupling element includes an optical window adapted for inspection by the optical assembly therethrough. Preferably, the endoscope insertion assembly includes a pulling element operative for selectably inserting the optical assembly within the endoscope insertion tube. Additionally, the pulling element is detachably engaged with the coupling element for selectable detachment therefrom.

In accordance with yet another preferred embodiment of the present invention the endoscope insertion assembly includes a mechanical stopper operative to prevent the optical assembly from being pulled out and frontward of the endoscope insertion tube. Preferably, the endoscope insertion tube further includes an instrument channel. Additionally, the endoscope insertion tube is a flexible endoscope insertion tube.

In accordance with still another preferred embodiment of the present invention the endoscope insertion tube is generally fluid impermeable.

There is thus provided in accordance with another preferred embodiment of the present invention an endoscope insertion assembly for performing endoscopy, including an endoscope insertion tube for passage through a body cavity, and an optical assembly for inspection of the body cavity, the optical assembly being selectably removable from the endoscope insertion tube. Additionally, the optical assembly is selectably insertable within the endoscope insertion tube.

There is thus provided in accordance with yet another preferred embodiment of the present invention a method for preparing an endoscope insertion assembly for performing endoscopy, including providing the endoscope insertion assembly including an endoscope insertion tube operative for passage through a body cavity, and an optical assembly operative for inspection of the body cavity, and selectably inserting the optical assembly within the endoscope insertion tube.

In accordance with a preferred embodiment of the present invention the method includes inspecting the body cavity employing the endoscope insertion assembly. Additionally, the method includes removing the optical assembly from the endoscope insertion tube following the inspection. Preferably, the method includes engaging the optical assembly with the endoscope insertion tube by employing a coupling element.

In accordance with another preferred embodiment of the present invention inspecting the body cavity is performed via an optical window. Preferably, the method includes isolating the optical assembly from fluids external to the endoscope insertion assembly. Additionally, inserting is performed by a pulling element operative for selectably inserting the optical assembly within the endoscope insertion tube.

In accordance with yet another preferred embodiment of the present invention the pulling element is detachably engaged with the coupling element for selectable detachment therefrom. Preferably, the method includes preventing the optical assembly from being pulled out and frontward of the endoscope insertion tube by employing a mechanical stopper.

BRIEF DESCRIPTION OF THE DRAWINGS

The present invention will be best understood and appreciated from the following detailed description, taken in conjunction with the drawings in which:

FIGS. 1A-1E are a simplified pictorial illustration of an optical assembly of an endoscopy system, a simplified side view illustration, a simplified front view illustration, a simplified sectional illustration taken along lines ID-ID in FIG. 1C and a simplified sectional illustration taken along lines IE-IE in FIG. 1C, respectively, constructed and operative in accordance with an embodiment of the present invention;

FIGS. 2A-2D are a simplified pictorial illustration of a coupling element of an endoscopy system, a simplified side view illustration, a simplified front view illustration and a simplified sectional illustration taken along lines IID-IID in FIG. 2C, respectively, constructed and operative in accordance with an embodiment of the present invention;

FIGS. 3A-3F are a simplified pictorial illustration of a pulling element of an endoscopy system, a simplified top view illustration, a simplified front view illustration, a simplified back view illustration, a simplified side view illustration and a simplified sectional illustration taken along lines IIIF-IIIF in FIG. 3C, respectively, constructed and operative in accordance with an embodiment of the present invention;

FIGS. 4A-4E are a simplified pictorial illustration of an endoscope insertion tube of an endoscopy system, a simplified side view illustration, a simplified front view illustration, a simplified sectional illustration taken along lines IVD-IVD in FIG. 4C and a simplified sectional illustration taken along lines IVE-IVE in FIG. 4C, respectively, constructed and operative in accordance with an embodiment of the present invention;

FIGS. 5A-5E are a simplified pictorial illustration of the endoscope insertion tube of FIGS. 4A-4E engaged with the coupling element of FIGS. 2A-2D and the pulling element of FIGS. 3A-3F, a simplified top view illustration, a simplified front view illustration, a simplified side view illustration and a simplified sectional illustration taken along lines VE-VE in FIG. 5C, respectively, constructed and operative in accordance with an embodiment of the present invention;

FIGS. 6A-6F are a simplified operational illustration of the endoscope insertion tube mounted on the coupling element and the pulling element, as shown in FIGS. 5A-5E, and the optical assembly of FIGS. 1A-1E at an initial advancing stage, a simplified top view illustration, a simplified front view illustration, a simplified side view illustration, a simplified sectional illustration taken along lines VIE-VIE in FIG. 6C and a simplified sectional illustration taken along lines VIF-VIF in FIG. 6C, respectively, constructed and operative in accordance with an embodiment of the present invention;

FIGS. 7A-7F are a simplified operational illustration of the endoscope insertion tube, the coupling element, the pulling element and the optical assembly of FIGS. 6A-6F at an intermediate advancing stage, a simplified top view illustration, a simplified front view illustration, a simplified side view illustration, a simplified sectional illustration taken along lines VIIE-VIIE in FIG. 7C and a simplified sectional illustration taken along lines VIIF-VIIF in FIG. 7C, respectively, constructed and operative in accordance with an embodiment of the present invention;

FIGS. 8A-8F are a simplified operational illustration of the endoscope insertion tube, the coupling element, the pulling element and the optical assembly of FIGS. 7A-7F at a final advancing stage, a simplified top view illustration, a simplified front view illustration, a simplified side view illustration, a simplified sectional illustration taken along lines VIIIE-VIIIE in FIG. 8C and a simplified sectional illustration taken along lines VIIIF-VIIIF in FIG. 8C, respectively, constructed and operative in accordance with an embodiment of the present invention;

FIGS. 9A-9F are a simplified operational illustration of the pulling element disengaged from the endoscope insertion tube, the coupling element and the optical assembly of FIGS. 8A-8F, a simplified top view illustration, a simplified front view illustration, a simplified side view illustration, a simplified sectional illustration taken along lines IXE-IXE in FIG. 9C and a simplified sectional illustration taken along lines IXF-IXF in FIG. 9C, respectively, constructed and operative in accordance with an embodiment of the present invention;

FIGS. 10A-10E are a simplified operational illustration of the endoscope insertion tube, the coupling element and the optical assembly of FIGS. 9A-9F, a simplified front view illustration, a simplified side view illustration, a simplified sectional illustration taken along lines XD-XD in FIG. 10B and a simplified sectional illustration taken along lines XE-XE in FIG. 10B, respectively, constructed and operative in accordance with an embodiment of the present invention;

FIGS. 11A-11E are a simplified operational illustration of the endoscope insertion tube disengaged from the coupling element and the optical assembly of FIGS. 10A-10E, a simplified front view illustration, a simplified side view illustration, a simplified sectional illustration taken along lines XID-XID in FIG. 11B and a simplified sectional illustration taken along lines XIE-XIE in FIG. 11B, respectively, constructed and operative in accordance with an embodiment of the present invention; and FIGS. 12A-12E are a simplified operational illustration of the coupling element disengaged from the optical assembly of FIGS. 11A-11E, a simplified front view illustration, a simplified side view illustration, a simplified sectional illustration taken along lines XIID-XIID in FIG. 12B and a simplified sectional illustration taken along lines XIIE-XIIE in FIG. 12B, respectively, constructed and operative in accordance with an embodiment of the present invention.

DETAILED DESCRIPTION OF EMBODIMENTS

The terms "endoscope" and "endoscopy" are used throughout in a manner somewhat broader than their customary meaning and refer to apparatus and methods which operate within body cavities, passageways and the like, such as, for example, the small intestine, the large intestine, arteries and veins. Although these terms normally refer to visual inspection, as used herein, they are not limited to applications which employ visual inspection and refer as well to apparatus, systems and methods which need not necessarily involve visual inspection.

The term "distal" refers to the remote end of an endoscope, accessory or tool furthest from the operator.

The term "proximal" refers to the end portion of an endoscope, accessory or tool closest to the operator, typically outside an organ or body portion of interest.

Figure 1D:
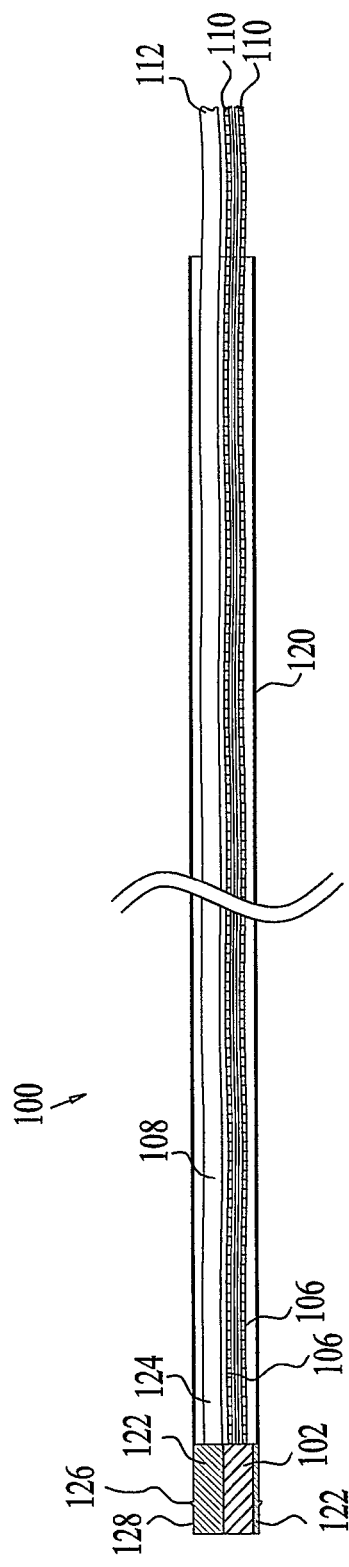

Reference is now made to FIGS. 1A-1E, which are a simplified pictorial illustration of an optical assembly of an endoscopy system, a simplified side view illustration, a simplified front view illustration, a simplified sectional illustration taken along lines ID-ID in FIG. 1C and a simplified sectional illustration taken along lines IE-IE in FIG. 1C, respectively, constructed and operative in accordance with an embodiment of the present invention. As seen in FIGS. 1A-1E an optical assembly 100 comprises optical elements that may include active and passive optical elements. The optical elements may include detection means 102 for light and/or image detection and illumination means 104.

The detection means 102 may be one or more of a Charged Coupled Device (CCD), a CMOS detector, array of optical fibers, a light guide or other detection means such as detection means used in standard endoscopy or other optical imaging systems. The illumination means 104 may be one or more of a Light Emitting Diode (LED), fiber optic illumination using one fiber or a bundle of fibers, a laser diode, or other means of optical illumination. Passive optical components that may be included in the optical assembly 100, and in particularly included in the detection means 102 and/or in the illumination means 104, may include any optical component, such as lenses, windows, mirrors, optical stops, and opto-mechanical assemblies with a plurality of optical components.

Figure 1E:
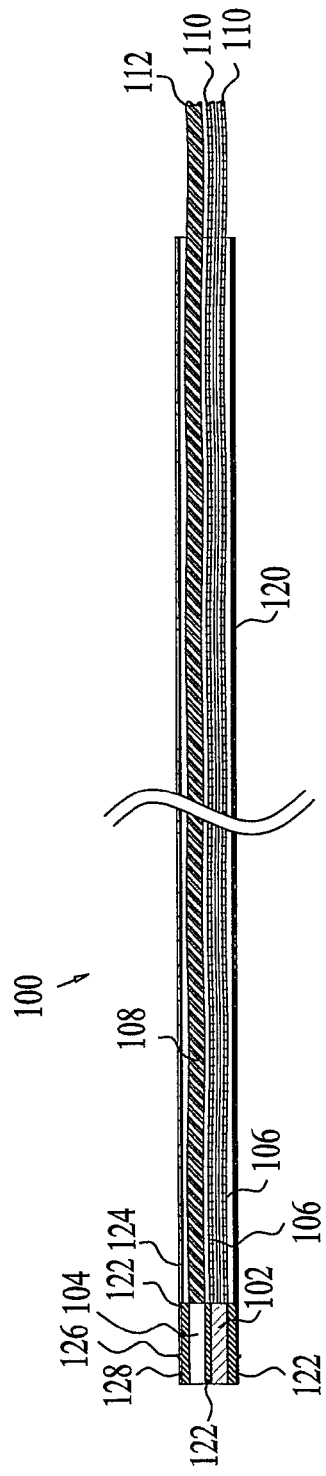

As seen in FIGS. 1D and 1E, data conduits 106 extend from the detection means 102 and illumination conduits 108 extend from the illumination means 104. The data conduits 106 of the detection means 102 may include means for operating the detection means 102 such as electrical wires for operating voltage and synchronization signals, and may also include wires for delivery of data detected from the signals, such as electrical wires for data transfer, or fibers for light detection, and may also include other conduits required to deliver the data to and from the detection means 102. The data conduits may also include means for electrical noise reduction and mechanical and electrical durability. The illumination conduits 108 of the illumination means 104 may include electrical wires for control and operation of the light source as in the case of a LED or a laser diode, or optical fibers for transmission of light, or a light guide, or any other means of operating and emitting light from the illumination means 104.

Both the data conduits 106 and the illumination conduits 108 may also include means for electrical noise reduction, temperature management, mechanical and electrical durability and other means generally required for electrical and mechanical components and conduits. The detection means 102 may be a conventional CCD such as a FTF2020M CCD commercially available from Dalsa Corporation, of 605 McMurray Rd., Waterloo, Ontario, Canada. The illumination means 104 may be a conventional LED, such as a L3-W34N-BR LED commercially available from Sloan AG of Basle, Switzerland.

Data conduits 106 and illumination conduits 108 may connect to a conventional endoscopy console (not shown) at respective end portions 110 and 112 thereof, via a console interface or a dedicated interface (not shown), as well known in the art. The endoscopy console may include, for example, a CV-100 video system center, a CLV-U20 light source, a SONY PVM-2030 video monitor, and an OFP flushing pump, all commercially available from Olympus America Inc. of 2 Corporate Center Drive, Melville, N.Y. 11747, USA, or a EPK-1000 video processor and a SONY LMD-2140MD medical grade flat panel LCD monitor, all commercially available from Pentax Europe GmbH, 104 Julius-Vosseler St., 22527 Hamburg, Germany.

It is noted that a single illumination means 104 or multiplicity of illumination means 104 may be employed. Additionally, a multiplicity of detection means 102 may be employed.

Data conduits 106 and illumination conduits 108 may be enclosed within a generally cylindrical housing 120 operative to enclose electrical wires 106 and light guide 108. Housing 120 may be constructed of a thin and flexible material, such as a thin TEFLON®, silicone, or PVC tube, thereby providing flexibility and bendability to optical assembly 100, as will be further described hereinbelow with reference to FIGS. 6A-12E. Housing 120 may be further operative to electrically shield electrical wires 106 and light guide 108. Housing 120 may be formed of a metallic shielding wire mesh, such as a Medical Braiding product manufactured by New England Catheter Corporation, of 130 North Main Street, Lisbon, N.H., USA, or Clear Braided PVC Tubing (catalog number 8601) manufactured by Capital Rubber Corporation, of 701 Frontier Way, Bensenville, Ill., USA. Housing 120 may be operative to enhance rigidity of optical assembly 100 so as to allow optical assembly 100 to be pulled and be selectively positioned within an endoscope insertion tube as will be further described hereinbelow with reference to FIGS. 6A-12E.

A generally cylindrical enclosing element 122 may extend from an end portion 124 of housing 120. Enclosing element 122 is operative to encase detection means 102 and illumination means 104, to protect detection means 102 and illumination means 104 from an environment external to the optical assembly 100 and to allow positioning of the optical assembly 100 within an endoscope insertion tube, as will be further described hereinbelow with reference to FIGS. 6A-12E.

A generally circumferential protrusion 126 protrudes from an external surface 128 of enclosing element 122 and is provided to fit within a coupling element, as will be further described hereinbelow with reference to FIGS. 6A-12E. Enclosing element 122 may be, for example, formed of a rigid plastic, such as molded polycarbonate, or any another rigid material. Additionally, enclosing element 122 may be dye-cast around detection means 102 and illumination means 104, typically, by using an epoxy adhesive or any other suitable material.

It is appreciated that optical assembly 100 may be a single-use disposable optical assembly, or a multiple-use optical assembly.

Figure 2A:
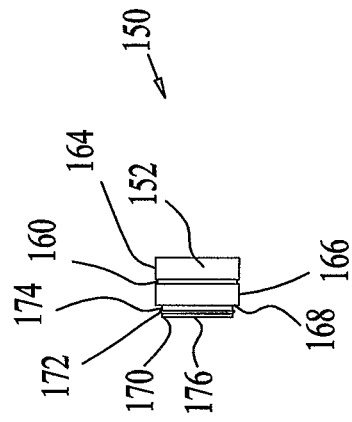
Figure 2B:
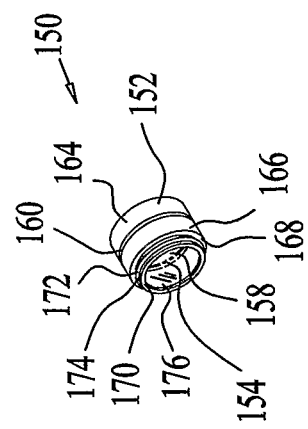

Reference in now made to FIGS. 2A-2D, which are a simplified pictorial illustration of a coupling element of an endoscopy system, a simplified side view illustration, a simplified front view illustration and a simplified sectional illustration taken along lines IID-IID in FIG. 2C, respectively, constructed and operative in accordance with an embodiment of the present invention. As seen in FIGS. 2A-2D a coupling element 150 is formed of a ring 152. A generally circumferential internal recess 154 extends along an internal surface 156 of a bore 158 defined by ring 152. Recess 154 may be provided to fit within protrusion 126 of optical assembly 100, as will be further described hereinbelow with reference to FIGS. 6A-12E.

A generally circumferential recess 160 extends along an external surface 164 of ring 152 and may be provided to fit within an endoscope insertion tube as will be further described hereinbelow with reference to FIGS. 8A-12E. On an end portion 166 of ring 152 is defined an external surface 168 adjacent to an end portion 170.

End portion 170 extends from ring 152 and defines a protrusion 172 with a generally triangular cross-section circumferentially extending along an external surface 174 of end portion 170. End portion 170 and protrusion 172 are provided to fit within a pulling element so as to allow tight engagement of coupling element 150 with the pulling element but to an extent that pulling element may be disengaged from coupling element 150 by selective exertion of force thereon, as will be further described hereinbelow with reference to FIGS. 5A-12E.

A wall 176 encloses end portion 170 and may be provided to function as an optical window so as to allow optical communication of detection means 102 and illumination means 104 or any other optical device comprised in optical assembly 100, with an environment external to optical assembly 100 during operation, such as in vivo inspection of the gastrointestinal tract, or other endoscopic procedures.

Wall 176 may be further provided to insulate optical assembly 100, and in particular, detection means 102 and illumination means 104 or any other optical device comprised in optical assembly 100, from an environment external to optical assembly 100. Wall 176 may be formed of any suitable material, such as a thin optically transparent glass or a plastic disc adhered to end portion 170 of coupling element 150. Alternatively, wall 176 may be formed as an integral part of coupling element 150, such as by forming coupling element 150 and wall 176 by optical injection molding of an optically transparent plastic, such as transparent polycarbonate, for example, or any other suitable material.

It is appreciated that coupling element 150 may be a single-use disposable coupling element, or a multi-use coupling element.

Reference is now made to FIGS. 3A-3F, which are a simplified pictorial illustration of a pulling element of an endoscopy system, a simplified top view illustration, a simplified front view illustration, a simplified back view illustration, a simplified side view illustration and a simplified sectional illustration taken along lines IIIF-IIIF in FIG. 3C, respectively, constructed and operative in accordance with an embodiment of the present invention.

As seen in FIGS. 3A-3F, pulling element 200 is comprised of a base portion 202. Base portion 202 is of a generally disc-like shape and is operative to couple with coupling element 150. Extending from base portion is a pulling wire 204, which is attached to a ring 210 at an opposite side of base portion 202. Ring 210 is provided to aid in pulling and advancing the pulling element 200 when coupled with the optical assembly 100 through coupling element 150, as will be further described hereinbelow with reference to FIGS. 6A-12E.

A generally circumferential aperture 220 is defined on a bottom surface 222 of base portion 202 so as to allow pulling element 200 to engage with coupling element 150 and optical assembly 100. An internal surface 224 is defined by aperture 220 within base portion 202.

Base portion 202 may be formed of any suitable material, such as any suitable metal or any suitable hard plastic, which may be injection-molded. Pulling wire 204 may be formed of flexible stainless-steel so as to provide high flexibility and bendability and enhanced pulling strength for pulling optical assembly 100 and coupling element 150 along a passageway in an endoscope insertion tube, as will be further described hereinbelow with reference to FIGS. 4A-4E and FIGS. 6A-12E. A highly flexible and bendable pulling wire 204 with substantial pulling strength is operative to be employed with a relatively long endoscope of an endoscope insertion tube (FIGS. 4A-4E), such as for gastrointestinal endoscopy, and which endoscope may be packed when not in use by being folded. Therefore a flexible pulling wire is preferably employed.

Alternatively, pulling wire 204 may be formed of a rigid material and may be employed with relatively short endoscopes.

Base portion 202 may be attached to pulling wire 204 by any suitable means, such as by being molded together, typically by insert-molding, whereas pulling wire 204 is inserted in a molding dye of base portion 202 prior to injection.

Base portion 202 and pulling wire 204 may be replaced by a tube (not shown) inserted within end portion 170 of coupling element 150 and fixed thereto by tight mounting of tube on protrusion 172 of coupling element 150. It is appreciated that pulling element 200 may be a single-use disposable pulling element, or a multiple-use pulling element.

Reference is now made to FIGS. 4A-4E, which are a simplified pictorial illustration of an endoscope insertion tube of an endoscopy system, a simplified side view illustration, a simplified front view illustration, a simplified sectional illustration taken along lines IVD-IVD in FIG. 4C and a simplified sectional illustration taken along lines IVE-IVE in FIG. 4C, respectively, constructed and operative in accordance with an embodiment of the present invention. As seen in FIGS. 4A-4E, an endoscope insertion tube 250 is comprised of a tube portion 252 with a generally ellipsoid-like shaped cross section. A passageway 254 is defined within a central lumen 256 of tube portion 252. A ring portion 260 extends from an end portion 262 of tube portion 252. On an internal surface 270 of a bore 272 defined within ring portion 260 is defined a generally circumferential recess 274.

Recess 274 may be provided to allow an O-ring 276 to be seated therein. O-ring 276 is provided to tightly engage endoscope insertion tube 250 with coupling element 150 by being partially seated within recess 274 of endoscope insertion tube 250 and partially seated within corresponding recess 160 of coupling element 150 (FIGS. 8E, 8F, 9E and 9F). O-ring 276 is preferably provided so as to allow tight engagement of coupling element 150 with endoscope insertion tube 250 but to an extent that endoscope insertion tube 250 may be disengaged from coupling element 150 by selective exertion of force on coupling element 150, as will be further described hereinbelow with reference to FIGS. 8A-10E. O-ring 276 may be operative to seal optical assembly 100 and insulate optical assembly 100 from an environment external to optical assembly 100, which environment may be a fluidic environment. A generally circumferential protrusion 280 protrudes from internal surface 270 of bore 272 and may be provided to operate as a mechanical stopper of the coupling element 150, as will be further described hereinbelow with reference to FIGS. 8A-9F.

A first throughgoing lumen 282 defined within ring portion 260 and tube portion 252 may operate as an accessory instrument channel 284. Instrument channel 284 may be provided for insertion of endoscopy accessories such as biopsy forceps, injection needles, polyp cutters, and any other endoscopy accessories as well known in the art.

Accessory instrument channel 284 may also be used for suction, as well known in the art A second throughgoing lumen 292 defined within ring portion 260 and tube portion 252 may operate as a channel 294 operative for water rinsing and air inflation, such as for intestinal insufflation forward of the endoscope, as common in endoscopy systems.

It is appreciated that ring portion 260 and tube portion 252 may assume any suitable cross sectional shape, and may comprise a multiplicity of lumens of various cross sections.

It is appreciated that a cross section of endoscope insertion tube 250, and specifically the cross sections of ring portion 260 and tube portion 252, may be of a circular shape or any other appropriate shape.

It is appreciated that endoscope insertion tube 250 may be a single-use disposable endoscope insertion tube, or a multiple-use endoscope insertion tube.

It is appreciated that the outer surface of endoscope insertion tube 250 is generally fluid impermeable, thereby preventing fluid passage therethrough and preventing contamination of bore 272 and optical assembly 100 when located therein, such as during endoscopic operation within a patient body, for example, as will be further describe with reference to FIGS. 7A-9F.

It is appreciated that endoscope insertion tube 250 may include additional components, channels and utilities as needed for performing an endoscopic procedure, such as steering wires or other steering assemblies (not shown) for steering the endoscope insertion tube within a body cavity or bending its distal tip portion, as well known in the art. Endoscope insertion tube 250 may further include an inflatable balloon at its distal portion, for example, to allow anchoring of endoscope insertion tube 250 to the internal walls of an inspected organ, such as the intestines, as described in detail in the above mentioned PCT patent applications PCT/IL2005/000152 and PCT/IL2005/000849 which are hereby incorporated by reference.

It is noted that the body cavity may include any body cavity, such as, for example, a cavity of the large intestine, the small intestine, the stomach, veins, arteries the urinal tract and the bronchi.

It is further appreciated that endoscope insertion tube may be flexible or rigid.

Figure 5D:
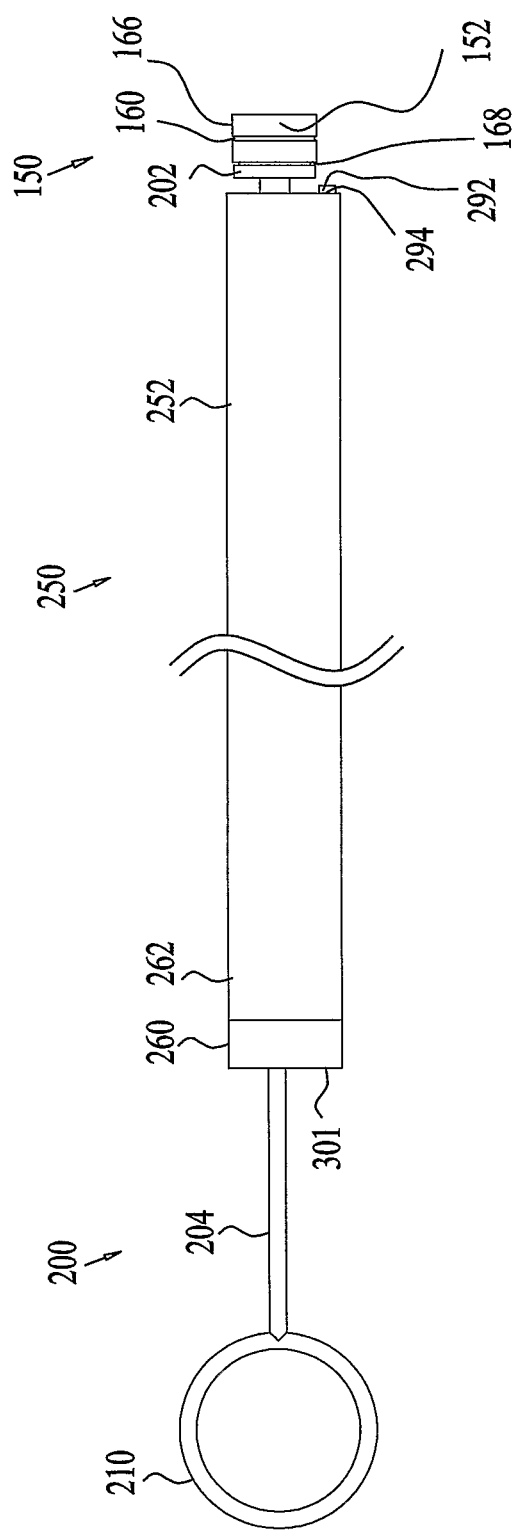
Figure 5E:
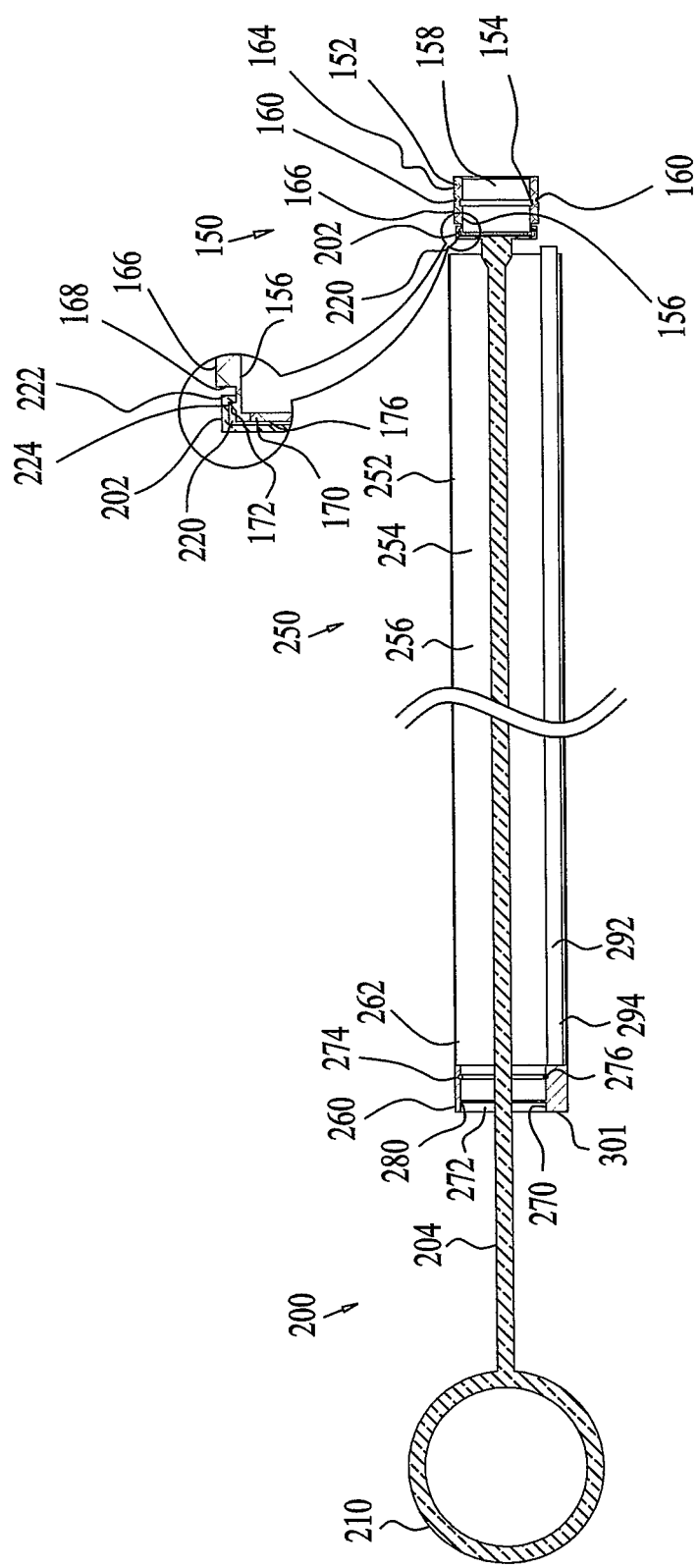

Reference is now made to FIGS. 5A-5E, which are a simplified pictorial illustration of the endoscope insertion tube of FIGS. 4A-4E engaged with the coupling element of FIGS. 2A-2D and the pulling element of FIGS. 3A-3F, a simplified top view illustration, a simplified front view illustration, a simplified side view illustration and a simplified sectional illustration taken along lines VE-VE in FIG. 5C, respectively, constructed and operative in accordance with an embodiment of the present invention.

As seen in FIGS. 5A-5E, the pulling wire 204 of pulling element 200 is at least partially inserted within the lumen 256 of tube portion 252 and bore 272 of ring portion 260 of the endoscope insertion tube 250. Preparation of an endoscope insertion assembly, inter alia, by insertion of pulling element 200 within endoscope insertion tube may be performed by any suitable manner, typically by manual insertion performed by an operator or by a production assembly worker, for example. End portion 170 of coupling element 150 is inserted within aperture 220 of base portion 202 of pulling element 200 and is secured within aperture 220 by protrusion 172 of coupling element 150. Protrusion 172 rests against internal surface 224 of base portion 202 and may operate as a mechanical stopper to prevent inadvertent detachment of pulling element 200 from coupling element 150. Pulling element 200 is provided for selectably inserting optical assembly 100 within endoscope insertion tube 250.

Figure 6A:
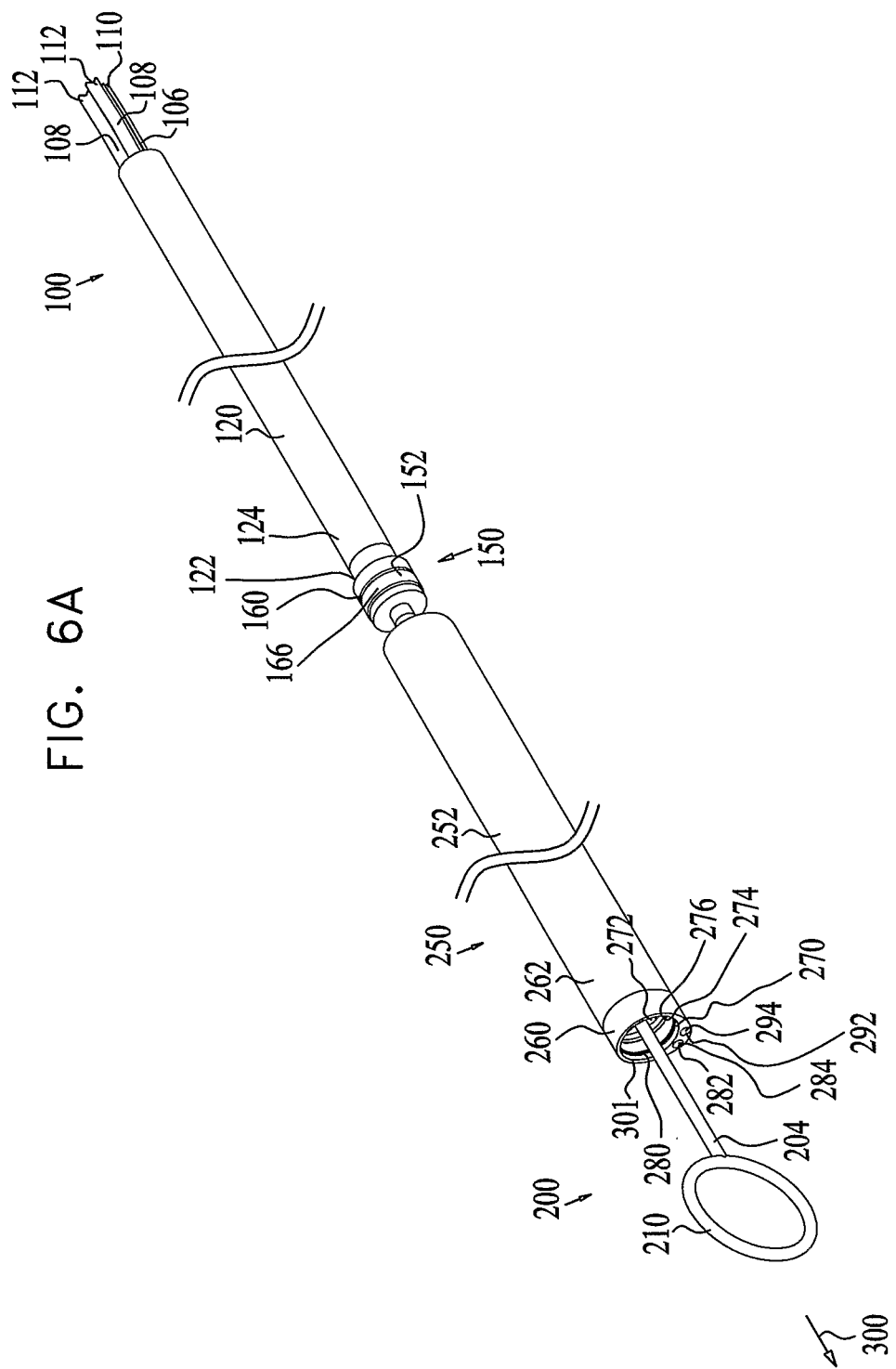
Figure 6D:
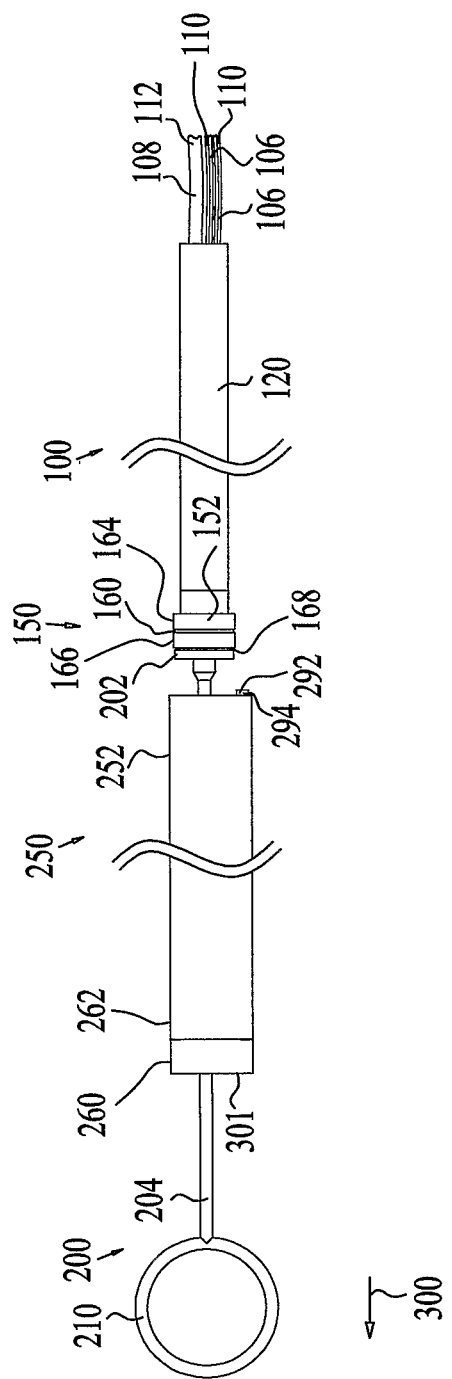
Figure 6E:
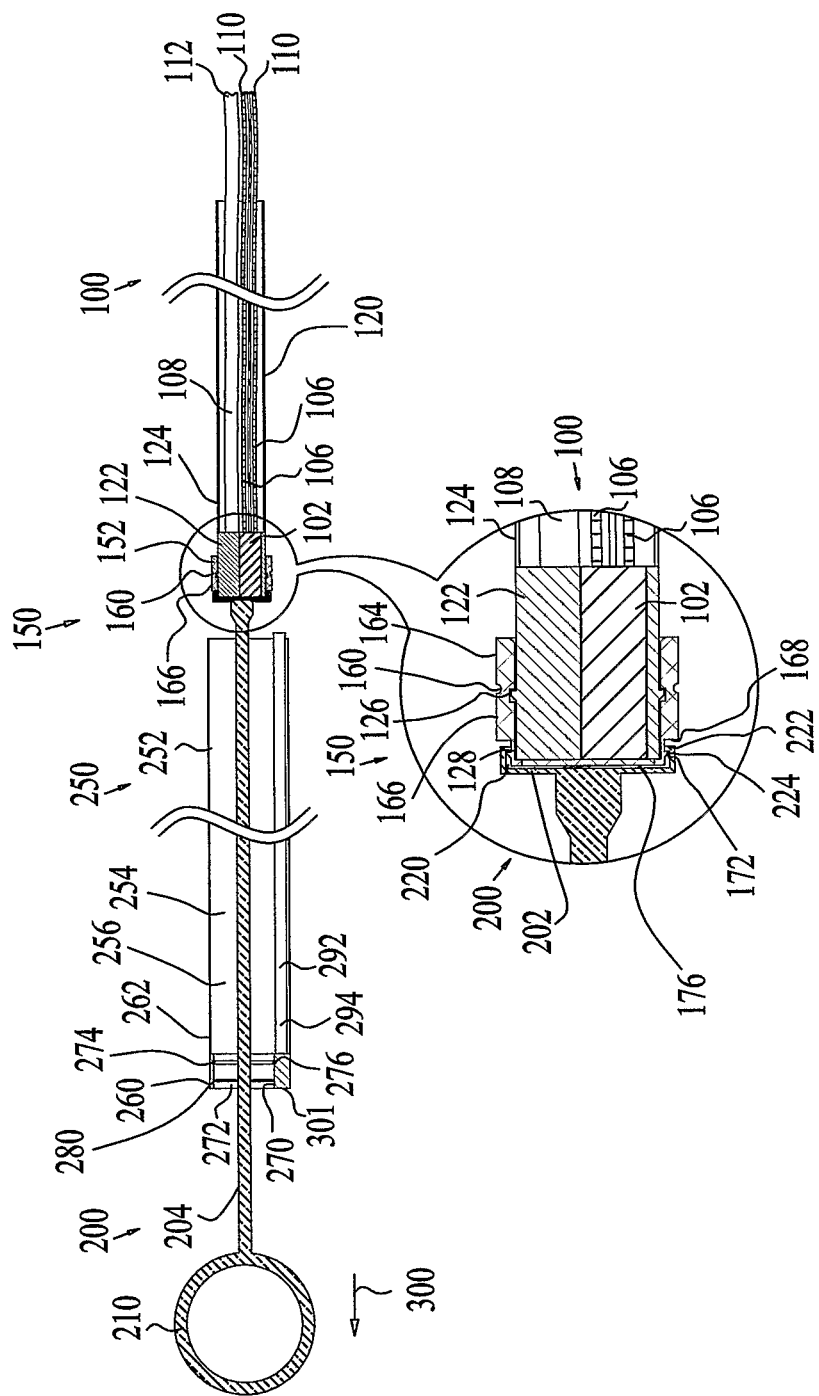
Figure 6F:
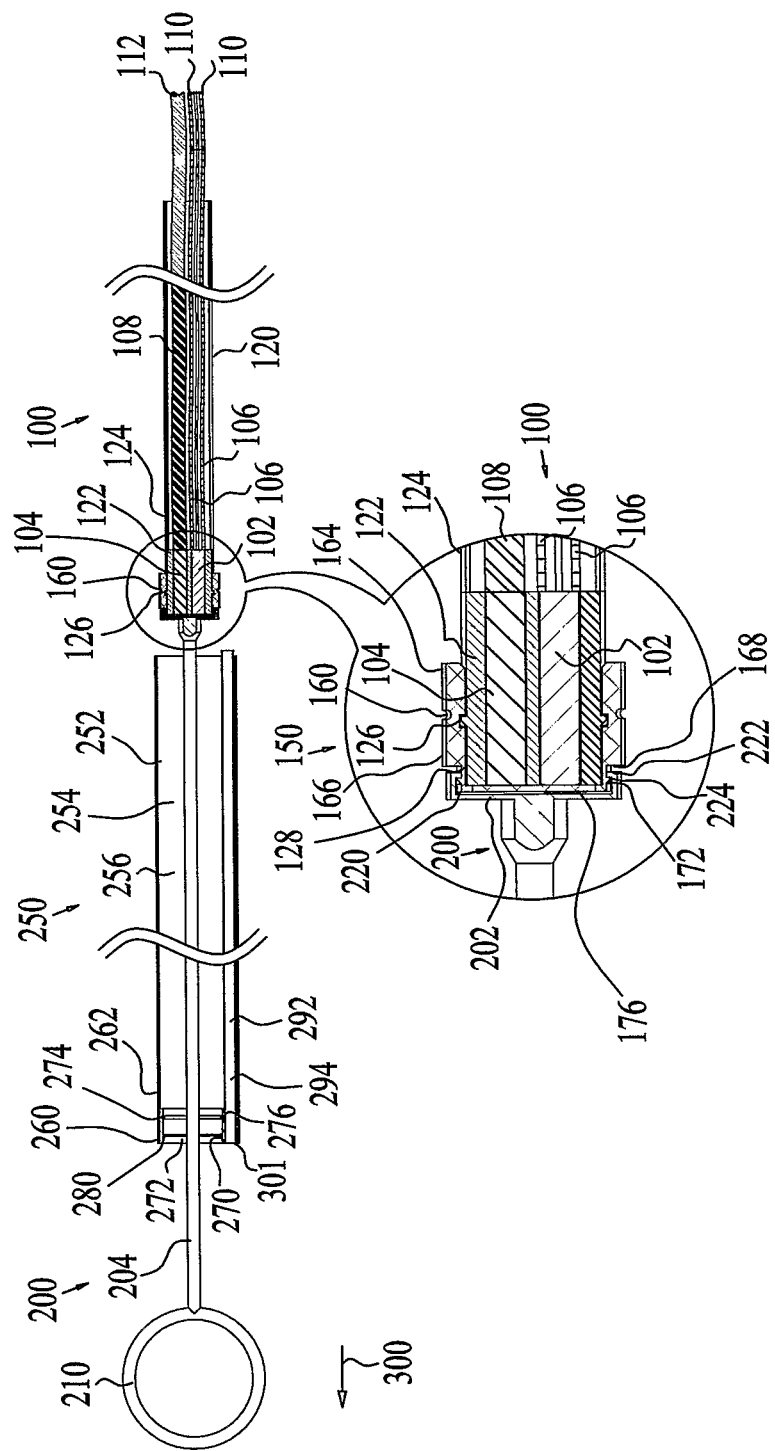

Reference is now made to FIGS. 6A-6F, which are a simplified operational illustration of the endoscope insertion tube mounted on the coupling element and the pulling element, as shown in FIGS. 5A-5E, and the optical assembly of FIGS. 1A-1E at an initial advancing stage, a simplified top view illustration, a simplified front view illustration, a simplified side view illustration, a simplified sectional illustration taken along lines VIE-VIE in FIG. 6C and a simplified sectional illustration taken along lines VIF-VIF in FIG. 6C, respectively, constructed and operative in accordance with an embodiment of the present invention.

As seen in FIGS. 6A-6F optical assembly 100 is coupled to pulling element 200 via coupling element 150 and pulling element 200 is detachably engaged with coupling element 150 for selectable detachment therefrom. Protrusion 126 of optical assembly 100 is seated within internal recess 154 of coupling element 150 so as to secure fitting of optical assembly 100 to coupling element 150. Pulling element 150 is operative to pull and advance optical assembly 100 within endoscope insertion tube 250 in a frontward direction, as indicated by an arrow 300, so as to position wall 176 of coupling element 150 in proximity to a front surface 301 of endoscope insertion tube 250, as will be further described hereinbelow with reference to FIGS. 8A-9F.

FIGS. 6A-6F show an initial operational stage prior to insertion of optical assembly 100 within endoscope insertion tube 250.

Optical assembly 100 is provided to be selectably insertable within passageway 254 of tube portion 252 and bore 272 of ring portion 260 of endoscope insertion tube 250 (FIGS. 7A-9F) during endoscopic operation so as to aid in performance of endoscopy, such as visual inspection within body cavities, passageways and the like, by means of the optical devices, such as the detection means 102 and the illumination means 104 comprised in optical assembly 100.

As seen in FIGS. 7A-9F, optical assembly 100 may be inserted within endoscope insertion tube 250 prior to endoscopic operation, by aid of coupling element 150 and pulling element 200, and may be extracted from endoscope insertion tube 250 following endoscopic operation, as seen in FIGS. 10A-12D.

It is a particular feature of the present invention that endoscope insertion tube 250 may be provided for one-time use during a single endoscopic operation and may be discarded following the single endoscopic operation. Optical assembly 100 may be employed in a multiplicity of endoscopic operations and therefore may be selectably inserted within endoscope insertion tube 250, prior to the endoscopic operation, and selectably detached, removed or extracted from endoscope insertion tube 250, following the endoscopic operation, so as to be employed in future endoscopic operations. This feature may be employed, for example, for eliminating the cleaning and/or sterilization of endoscope insertion tube 250 after an endoscopic operation, and/or whereas endoscope insertion tube 250 is generally inexpensive in comparison with optical assembly 100, which is generally costly.

Alternatively, optical assembly 100 may be provided for one-time use during a single endoscopic operation and may be discarded following the single endoscopic operation. Endoscope insertion tube 250 may be employed in a multiplicity of endoscopic operations and therefore a new optical assembly 100 may be inserted within endoscope insertion tube 50, prior to the endoscopic operation, and extracted from endoscope insertion tube 250, following the endoscopic operation. It is appreciated that in such a case endoscope insertion tube 250 may be operative to withstand cleaning, disinfecting or sterilization processes.

Single use of endoscope insertion tube 250 may enhance sterility of the endoscopic operation by providing a new, sterile endoscope insertion tube 250 to perform each endoscopic operation, thus obviating the need to reuse the endoscope insertion tube 250, which may come within direct contact with body cavities, passageways and the like during endoscopic operation.

Figure 7B:
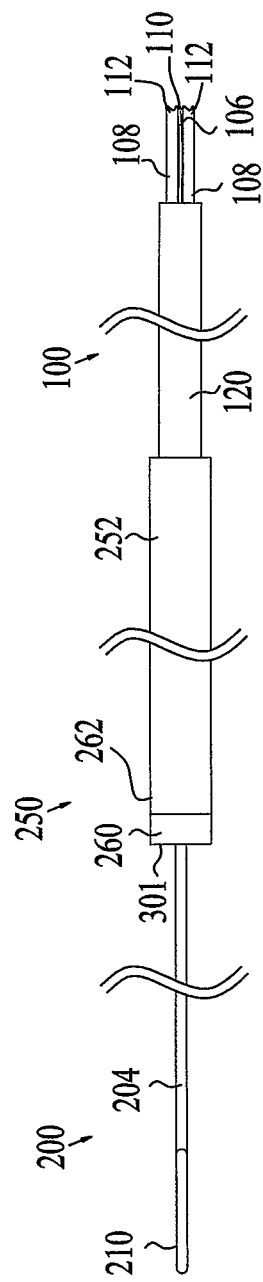
Figure 7C:
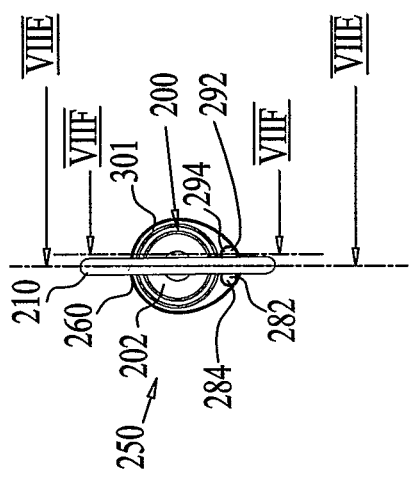
Figure 7D:
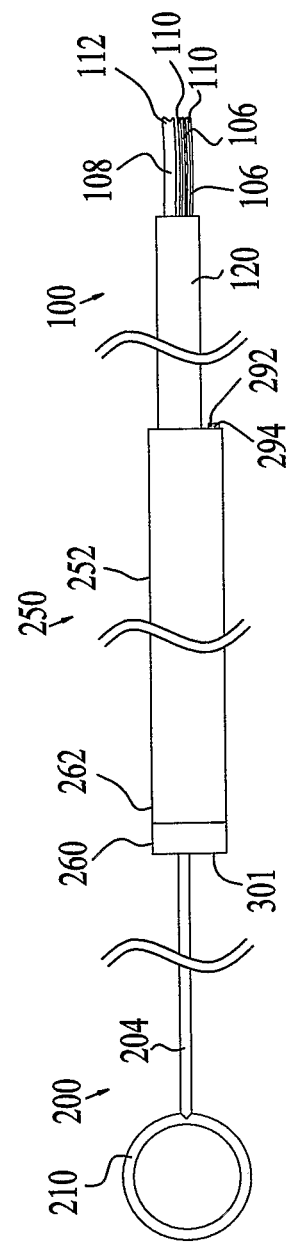
Figure 7E:
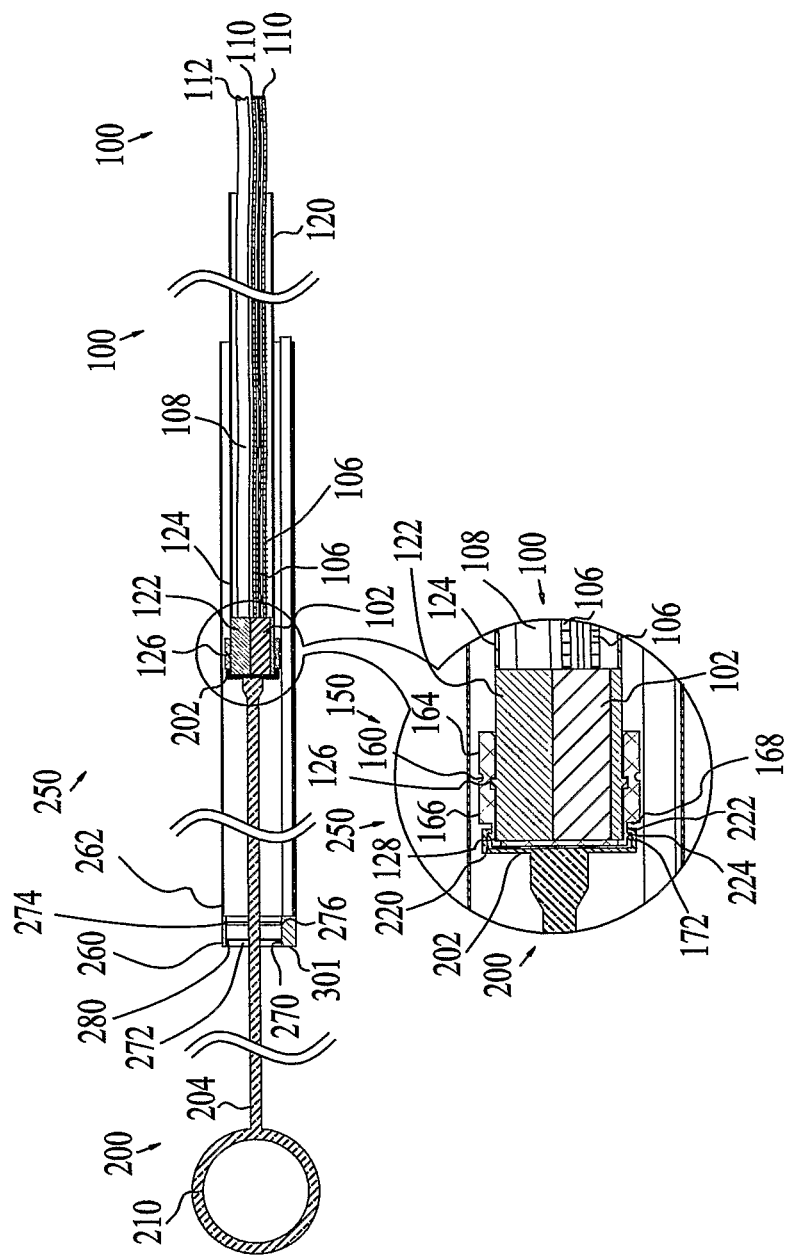
Figure 7F:
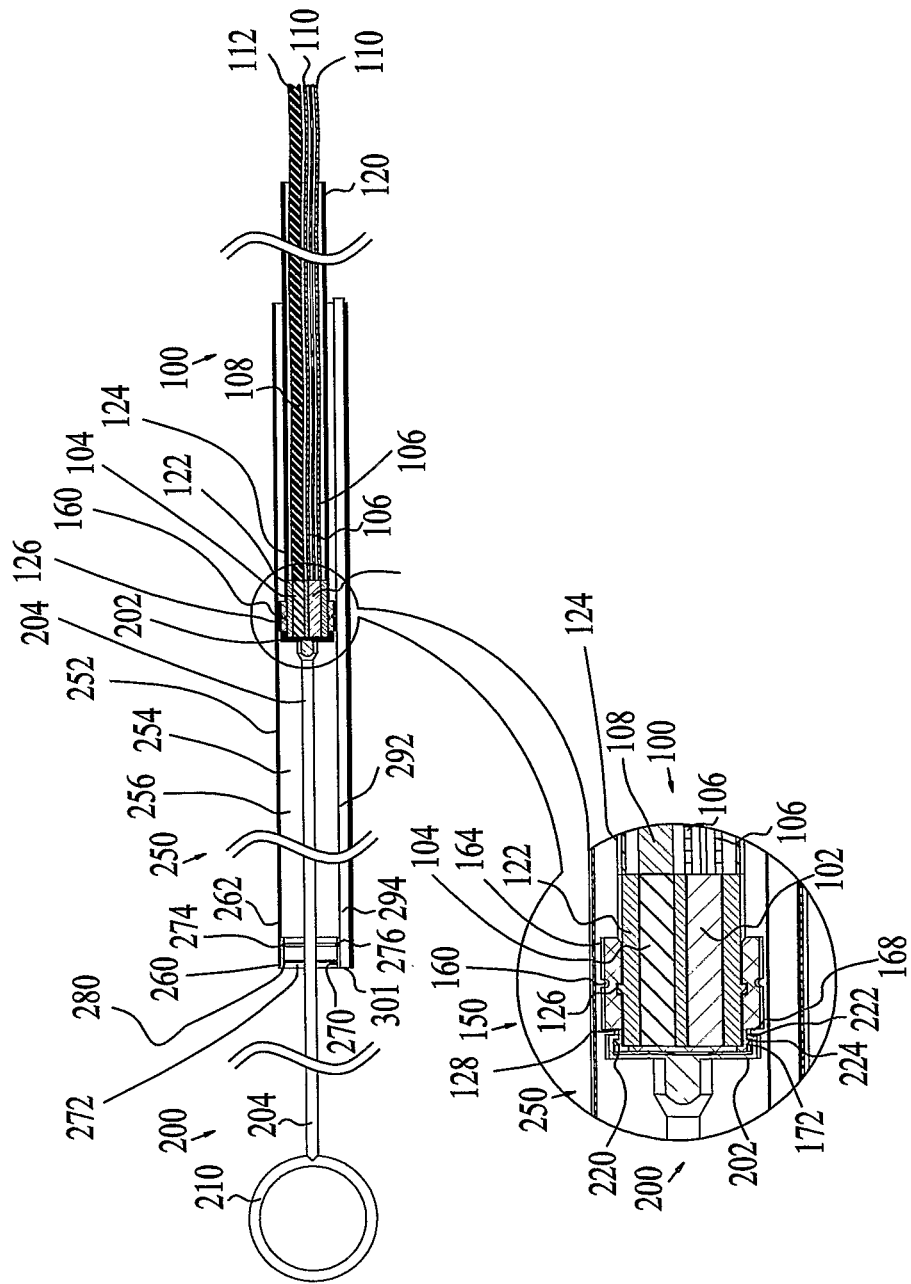

Reference is now made to FIGS. 7A-7F, which are a simplified operational illustration of the endoscope insertion tube, the coupling element, the pulling element and the optical assembly of FIGS. 6A-6F at an intermediate advancing stage, a simplified top view illustration, a simplified front view illustration, a simplified side view illustration, a simplified sectional illustration taken along lines VIIE-VIIE in FIG. 7C and a simplified sectional illustration taken along lines VIIF-VIIF in FIG. 7C, respectively, constructed and operative in accordance with an embodiment of the present invention.

In FIGS. 7A-7F pulling element 200 is shown to have partially advanced and position coupling element 150 and optical assembly 100 within tube portion 252 of endoscope insertion tube 250.

Figure 8A:
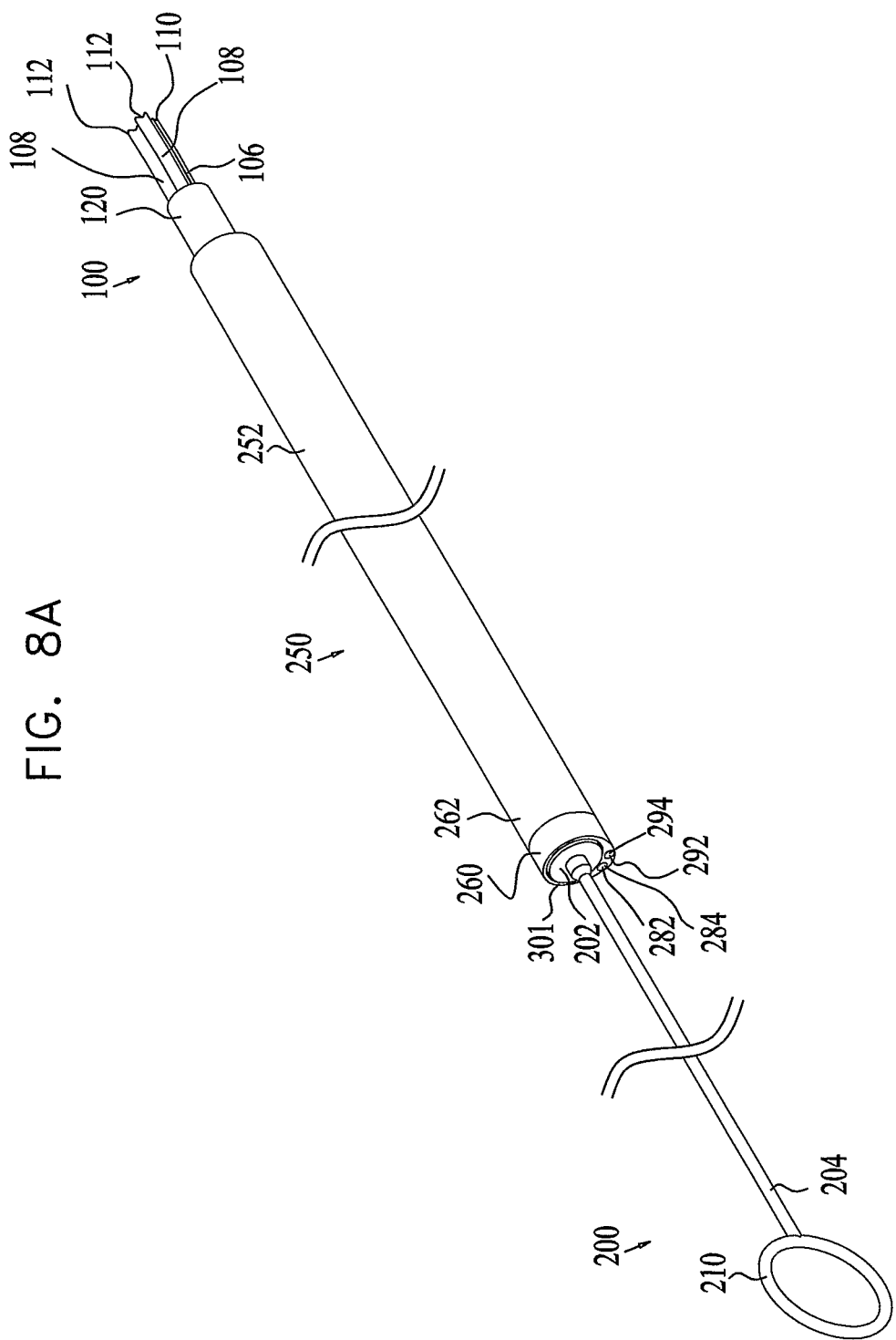
Figure 8B:
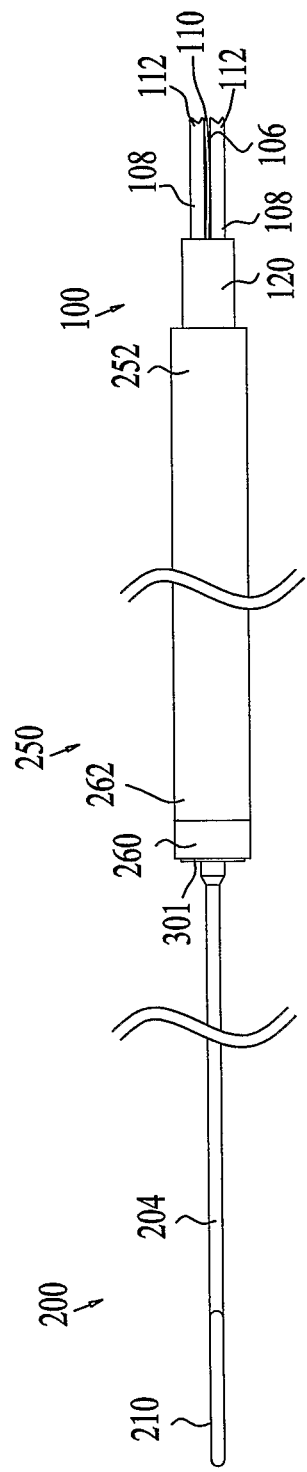
Figure 8C:
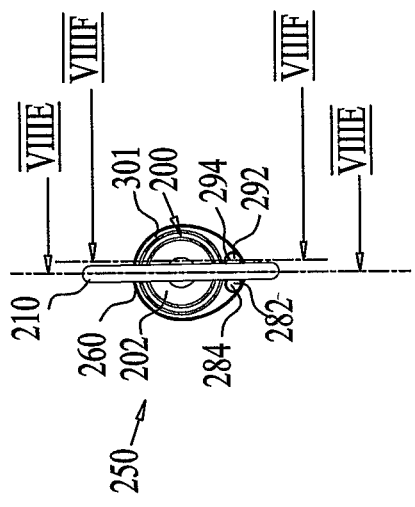

Reference is now made to FIGS. 8A-8F, which are a simplified operational illustration of the endoscope insertion tube, the coupling element, the pulling element and the optical assembly of FIGS. 7A-7F at a final advancing stage, a simplified top view illustration, a simplified front view illustration, a simplified side view illustration, a simplified sectional illustration taken along lines VIIIE-VIIIE in FIG. 8C and a simplified sectional illustration taken along lines VIIIF-VIIIF in FIG. 8C, respectively, constructed and operative in accordance with an embodiment of the present invention.

Figure 8E:
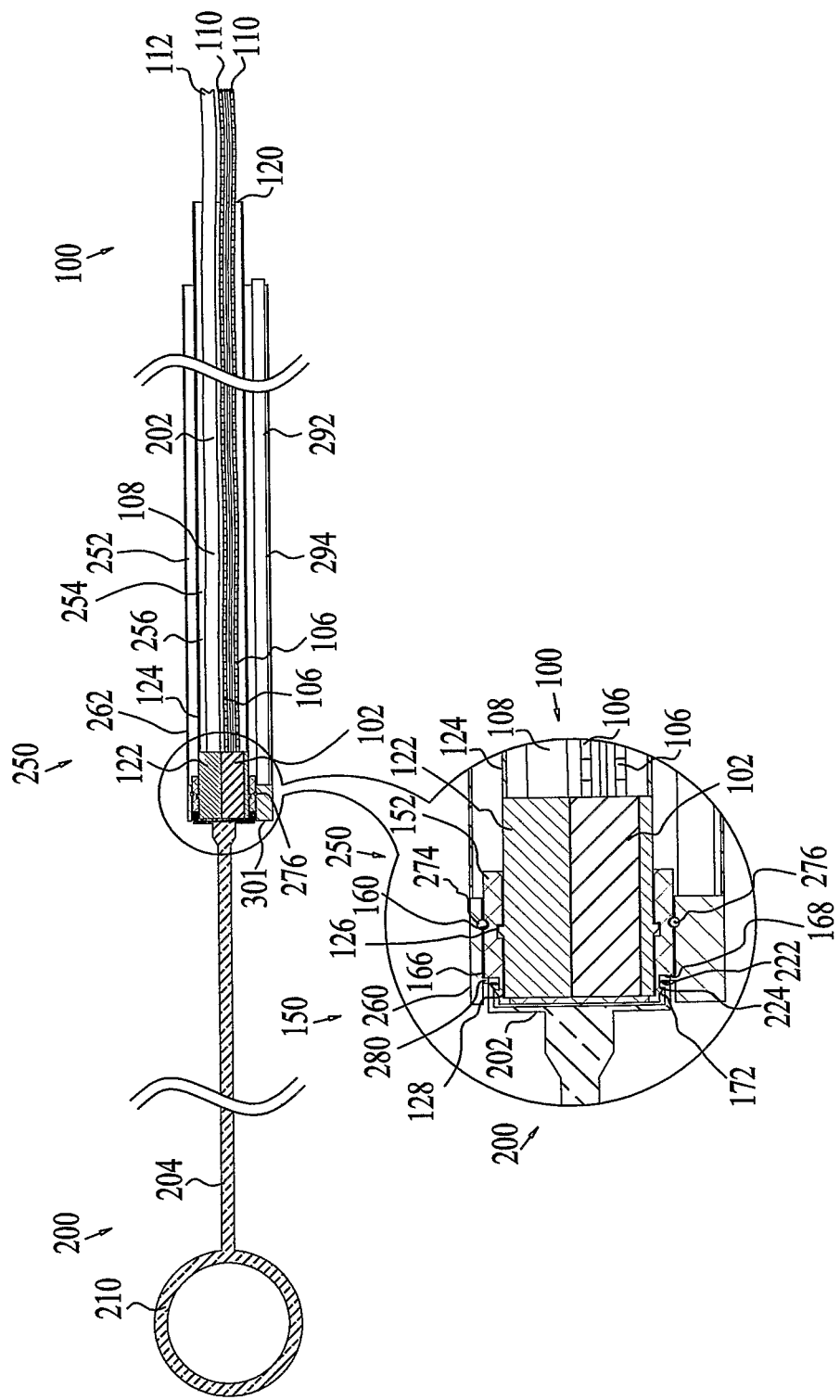
Figure 8F:
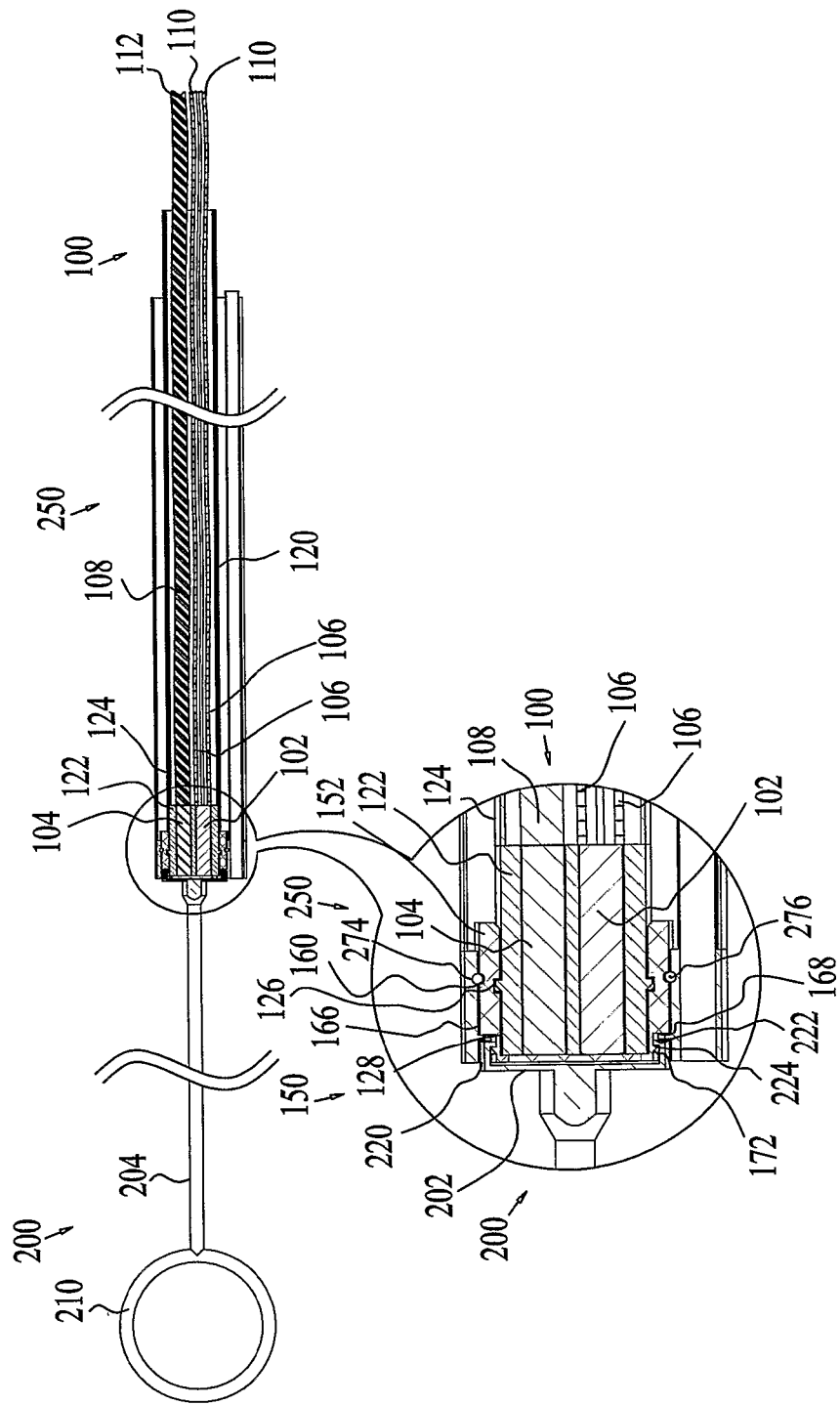

In FIGS. 8A-8F pulling element 200 is shown to have advanced and position coupling element 150 partially within bore 272 of ring portion 260 of endoscope insertion tube 250. Ring 152 of coupling element 150 is tightly engaged with ring portion 260 of endoscope insertion tube 250 by O-ring 276, which is partially seated within recess 274 of ring portion 260 and partially seated within corresponding recess 160 of ring 152. Positioning of coupling element 150 within endoscope insertion tube 250 is aided by protrusion 280 of endoscope insertion tube 250, which protrusion rests up and against external surface 168 of coupling element 150 (FIGS. 8E and 8F). Protrusion 280 operates as a mechanical stopper so as to prevent coupling element 150 from being pulled out and frontward of endoscope insertion tube 250, thereby preventing optical assembly 100 from being pulled out and frontward of endoscope insertion tube 250.

Figure 9A:
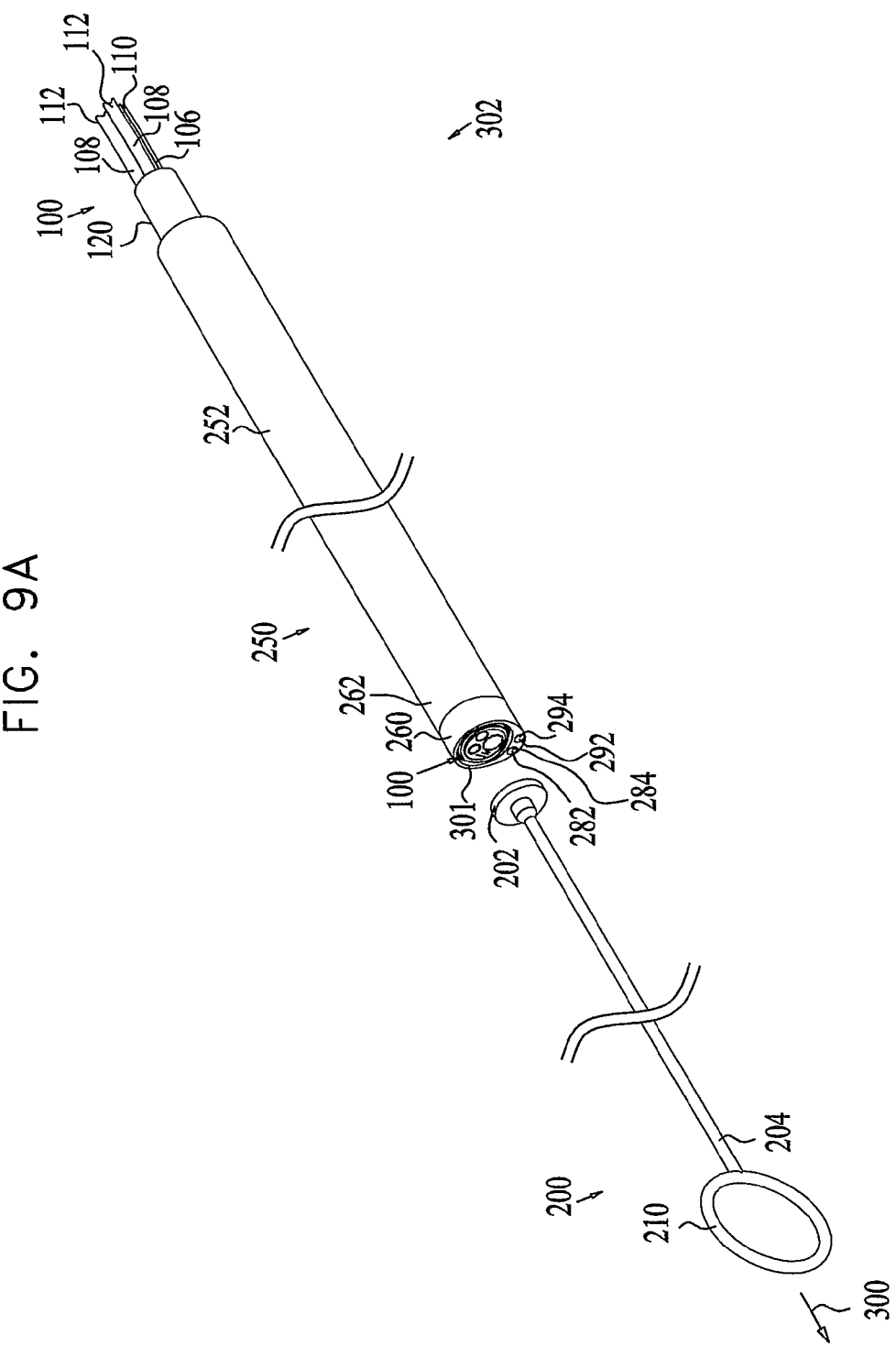
Figure 9D:
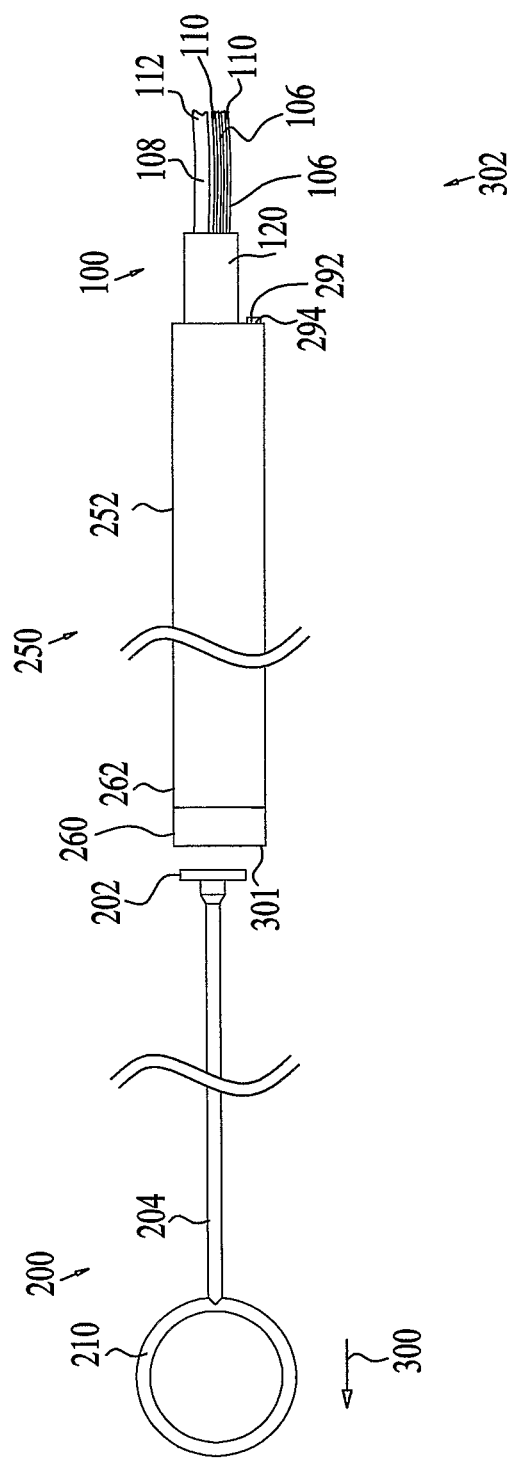
Figure 9E:
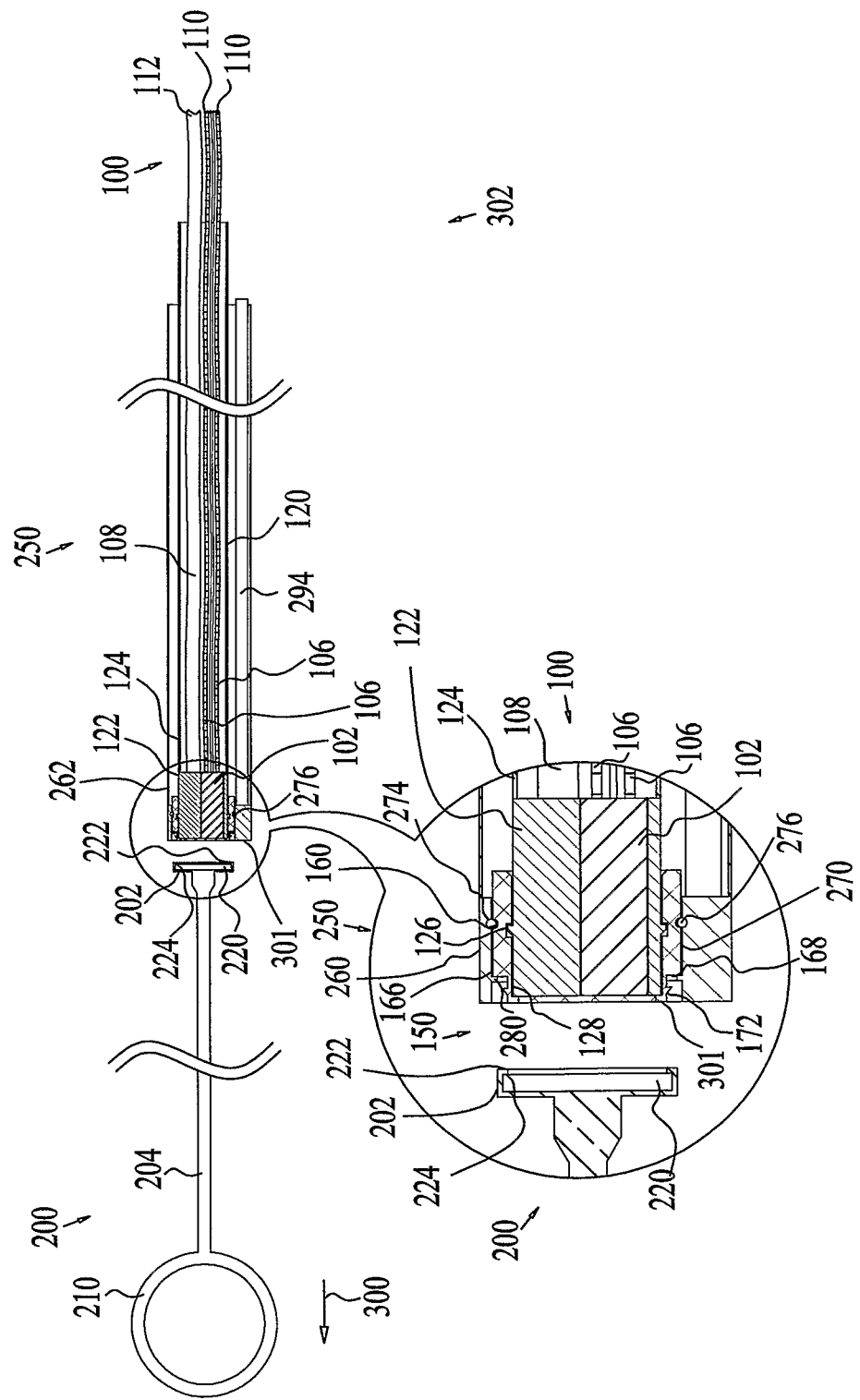
Figure 9F:
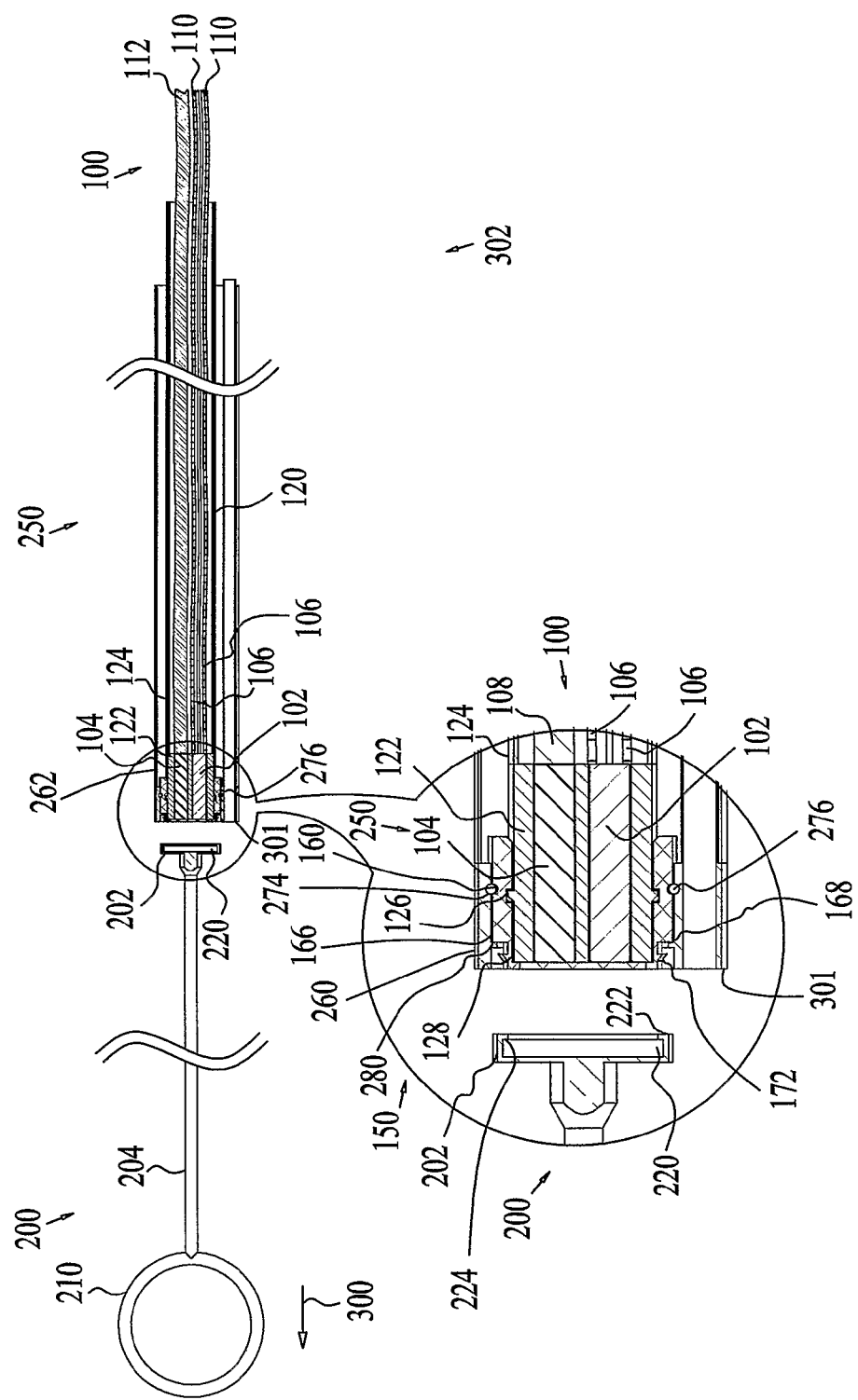

Reference is now made to FIGS. 9A-9F, which are a simplified operational illustration of the pulling element disengaged from the endoscope insertion tube, the coupling element and the optical assembly of FIGS. 8A-8F, a simplified top view illustration, a simplified front view illustration, a simplified side view illustration, a simplified sectional illustration taken along lines IXE-IXE in FIG. 9C and a simplified sectional illustration taken along lines IXF-IXF in FIG. 9C, respectively, constructed and operative in accordance with an embodiment of the present invention.

As seen in FIGS. 9A-9F, pulling element 200 is pulled frontward in the direction indicated by arrow 300 and is removed from coupling element 150 by release of internal surface 224 of base portion 202 of pulling element 200 from protrusion 172 of coupling element 150. The pulling of pulling element 150 may be performed by any suitable manner, typically by manual pulling performed by an operator, for example. Endoscope insertion tube 250 is shown to remain with coupling element 150 and optical assembly 100 inserted therein, thereby defining an endoscope insertion assembly 302 operative to perform endoscopic operations.

Figure 10B:
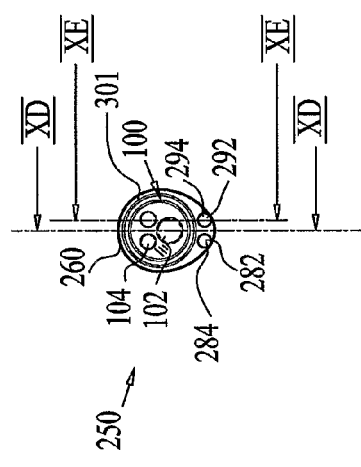
Figure 10C:
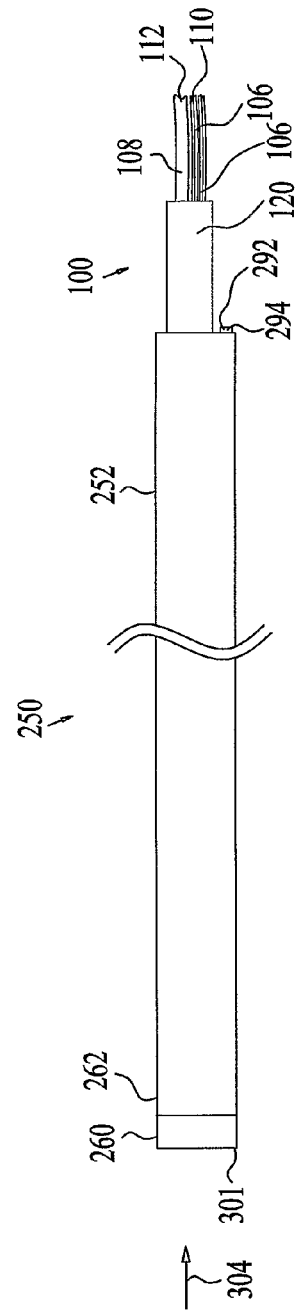

Reference is now made to FIGS. 10A-10E, which are a simplified operational illustration of the endoscope insertion tube, the coupling element and the optical assembly of FIGS. 9A-9F, a simplified front view illustration, a simplified side view illustration, a simplified sectional illustration taken along lines XD-XD in FIG. 10B and a simplified sectional illustration taken along lines XE-XE in FIG. 10B, respectively, constructed and operative in accordance with an embodiment of the present invention.

Figure 10D:
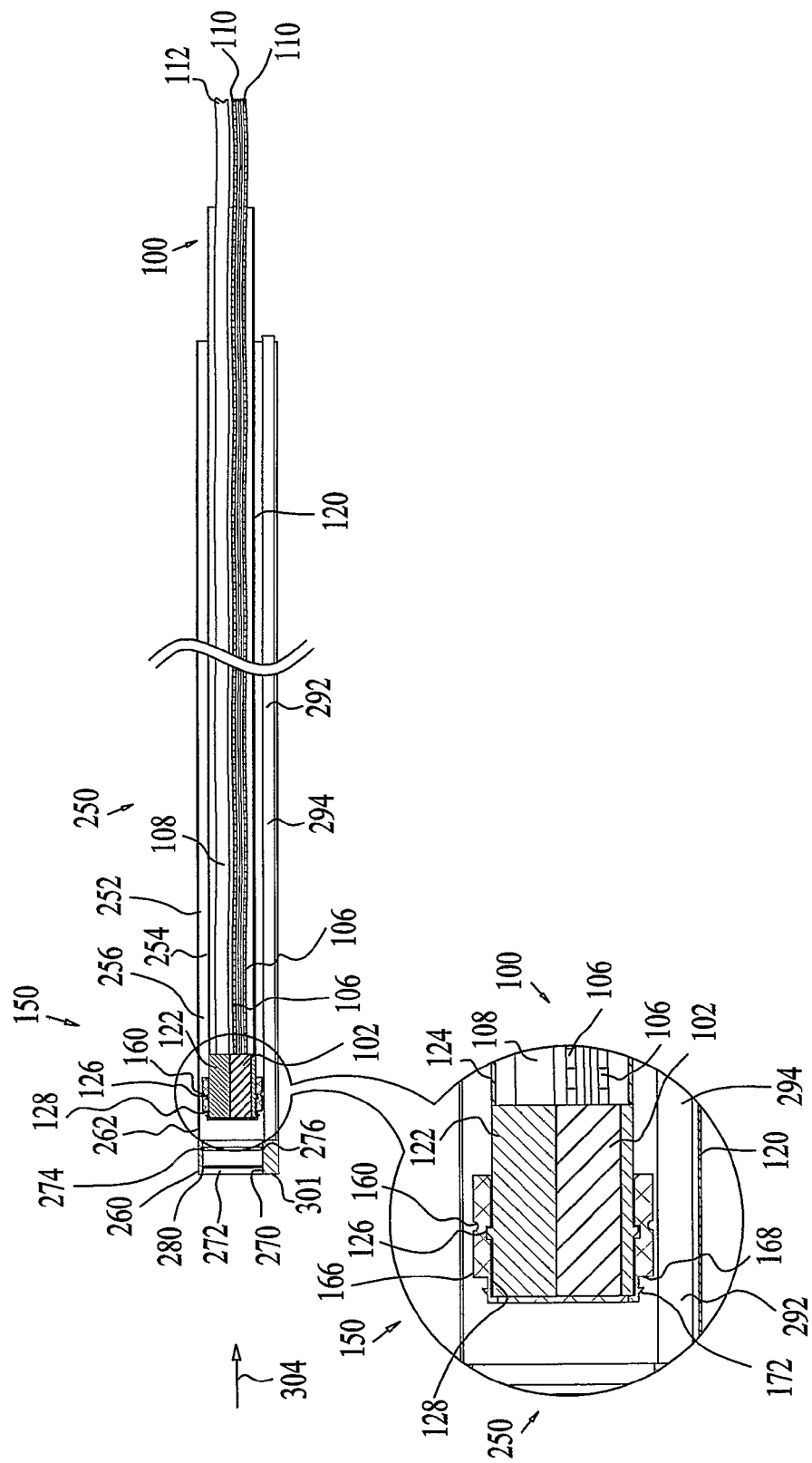

As seen in FIGS. 10A-10E, upon exertion of force on wall 176 of coupling element 150, in a rearward direction indicated by an arrow 304, coupling element 150 is extracted from ring portion 260 of endoscope insertion tube 250 by release of recess 160 from O-ring 276. In FIGS. 10D and 10E coupling element 150 and optical assembly 100 inserted therein, are shown to be positioned within passageway 254 of tube portion 252 of endoscope insertion tube 250. Exertion of force may be performed in any suitable manner, typically by manual force exertion performed by an operator, for example. Manual force exertion may be performed in any suitable manner, such as by directly pressing wall 176 with a finger or with the aid of a tool, such as a rod (not shown) with a diameter smaller than a cross section diameter of bore 272 of endoscope insertion tube 250.

Extraction of coupling element 150 and optical assembly 100 from ring portion 260 and eventually from endoscope insertion tube 250 (FIGS. 11A-12E) is performed to remove optical assembly 100 from endoscope insertion tube 250 following endoscopic operation, for example, for allowing the use of optical assembly 100 in future endoscopic operations while endoscope insertion tube 250 may be discarded following a single endoscopic operation or a few endoscopic operations.

Figure 11C:
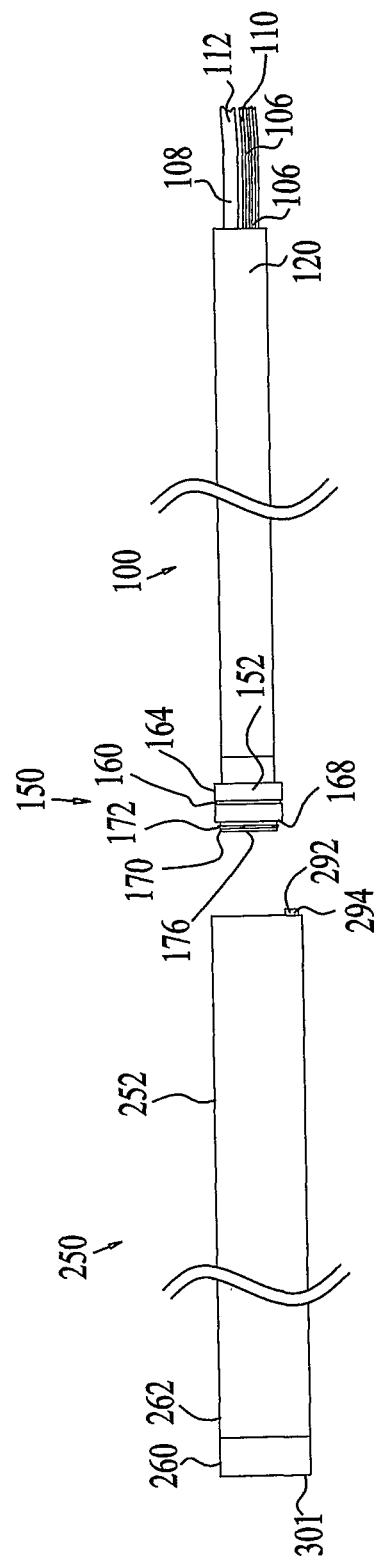
Figure 11D:
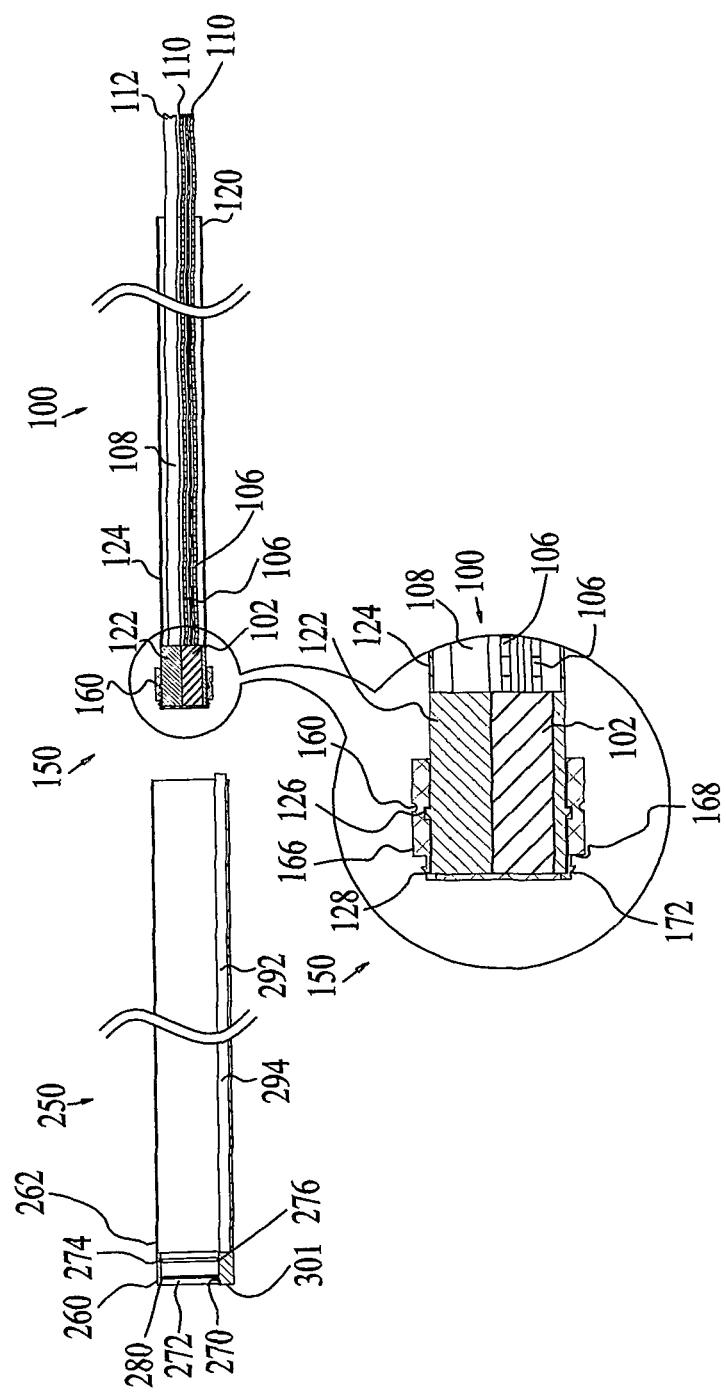
Figure 11E:
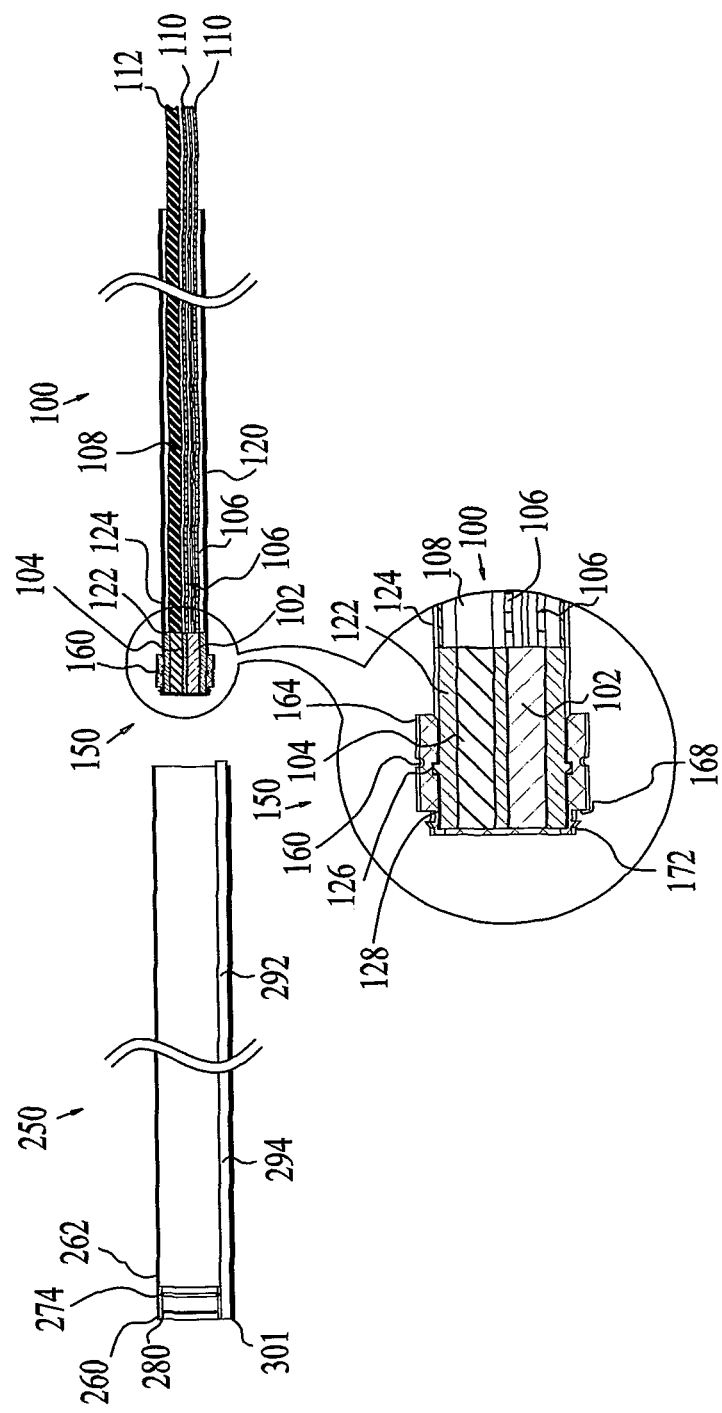

Reference is now made to FIGS. 11A-11E, which are a simplified operational illustration of the endoscope insertion tube disengaged from the coupling element and the optical assembly of FIGS. 10A-10E, a simplified front view illustration, a simplified side view illustration, a simplified sectional illustration taken along lines XID-XID in FIG. 11B and a simplified sectional illustration taken along lines XIE-XIE in FIG. 11B, respectively, constructed and operative in accordance with an embodiment of the present invention.

As seen in FIGS. 11A-11E, coupling element 150 and optical assembly 100 are completely extracted from endoscope insertion tube 250.

Figures 12A, 12B:
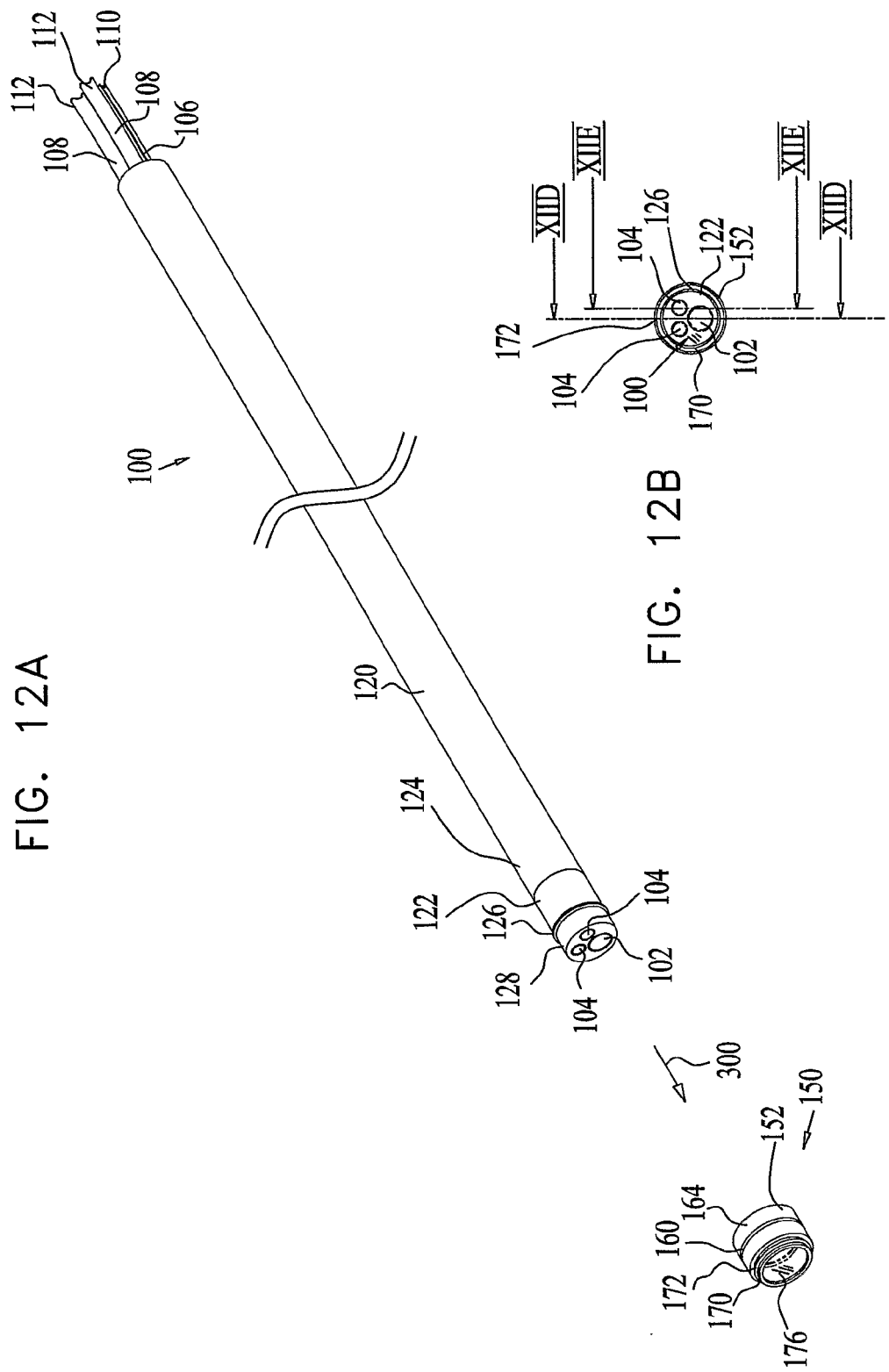
Figure 12E:
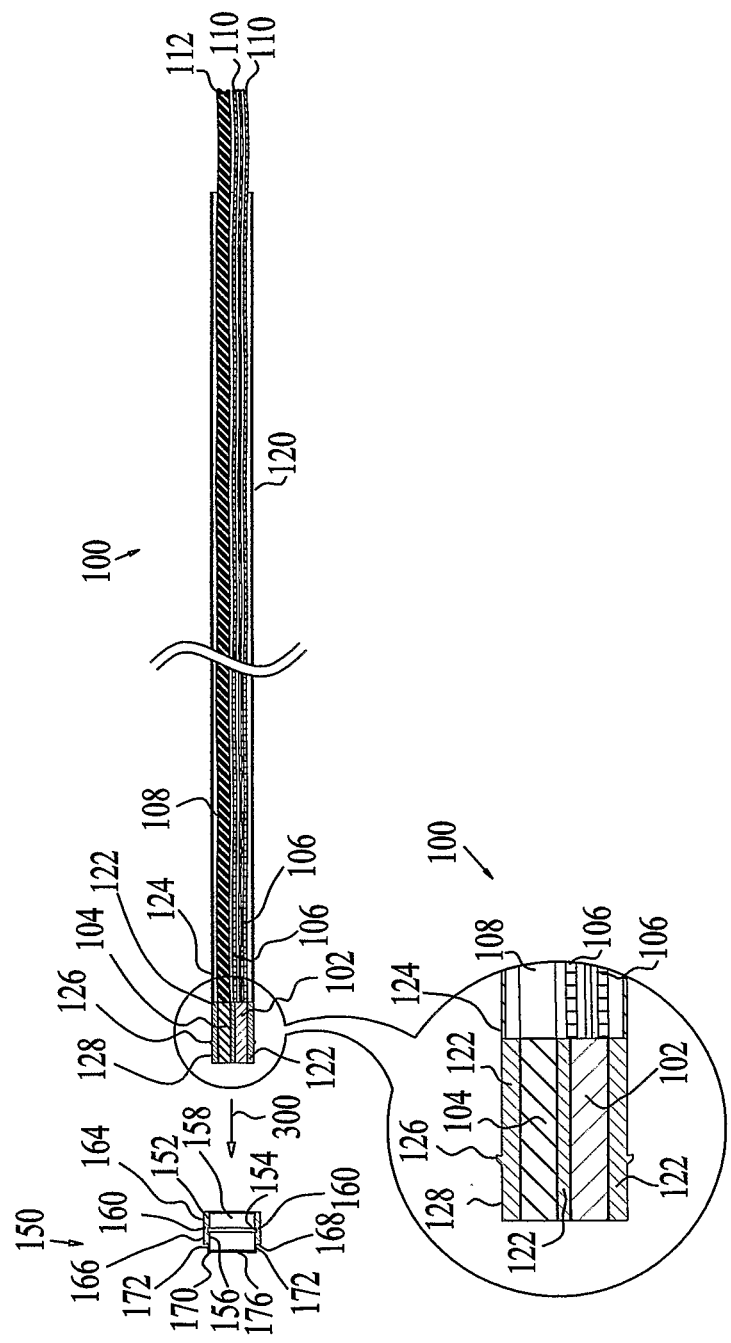

Reference is now made to FIGS. 12A-12E, which are a simplified operational illustration of the coupling element disengaged from the optical assembly of FIGS. 11A-11E, a simplified front view illustration, a simplified side view illustration, a simplified sectional illustration taken along lines XIID-XIID in FIG. 12B and a simplified sectional illustration taken along lines XIIE-XIIE in FIG. 12B, respectively, constructed and operative in accordance with an embodiment of the present invention.

As seen in FIGS. 12A-12E, upon exertion of force in a frontward direction indicated by arrow 300, coupling element 150 is removed from optical assembly 100 by release of protrusion 126 of optical assembly 100 from recess 160 of coupling element 150. Following removal of coupling element 150 from optical assembly 100, optical assembly 100 is operative to be used in future endoscopic operations. Coupling element 150 may be discarded.

It is appreciated that during an endoscopic operation with endoscope insertion assembly 302, as described hereinabove, the optical assembly 100 may remain isolated and separated from a body organ or a cavity undergoing an endoscopic operation and avoid contact with the body organ, cavity, with other body fluids or with any fluids external to the endoscope insertion assembly. It is further appreciated that by releasing optical assembly 100 from endoscope insertion tube 250 and coupling element 150 as described hereinabove, optical assembly 100 may remain clean and uncontaminated after the endoscopic operation.

It is yet appreciated that even in a case wherein optical assembly 100 is contaminated and unclean, an assembly comprising the endoscope insertion assembly 302 with the coupling element 150, as described hereinabove, prevents optical assembly 100 from contaminating the body organ or cavity undergoing the endoscopic operation, due to the isolation of optical assembly 100 from the body organ or cavity undergoing the endoscopic operation.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specifications and which are not in the prior art.

What is claimed is:

1. An endoscope insertion assembly for performing endoscopy, comprising:
   an endoscope insertion tube operative for passage through a body cavity and comprising:
   a distal end having an engagement portion for disengageable coupling engagement with an optical assembly;
   a proximal end; and
   at least one lumen extending through said endoscope insertion tube between said distal end and said proximal end;
   said optical assembly being operative for inspection of said body cavity and being selectably insertable within said endoscope insertion tube; and
   a pulling element operative for insertion through said at least one lumen of said endoscope insertion tube from said distal end thereof to said proximal end thereof, and comprising:
   a base portion at a first end of said pulling element;
   a handle portion at a second end of said pulling element, said second end being opposite said first end; and
   an interconnecting element interconnecting said base portion and said handle portion,
   said base portion being adapted for disengageable coupling engagement with said optical assembly, said handle portion being disposed distally with respect to said endoscope insertion tube, whereby when said base portion at said first end of said pulling element is slidably inserted into said lumen of said endoscope insertion tube from said distal end of said endoscope insertion tube, pushing said handle of said pulling element towards said distal end of said endoscope insertion tube slides said base portion at said first end of said pulling element from said distal end of said endoscope insertion tube towards said proximal end of said endoscope insertion tube in order to produce said coupling engagement of said base portion with said optical assembly and pulling said handle of said pulling element in a direction opposite to a direction of said pushing, causes said base portion to slide back towards said distal end of said endoscope insertion tube, thereby to pull said optical assembly into said lumen of said endoscope insertion tube and into said coupling engagement with said engagement portion of said distal end of said endoscope insertion tube.

2. An endoscope insertion assembly according to claim 1 and also comprising a coupling element operative for engaging said optical assembly with said endoscope insertion tube.

3. An endoscope insertion assembly according to claim 2 and wherein said endoscope insertion tube and said coupling element are operative to isolate said optical assembly from fluids external to said endoscope insertion assembly.

4. An endoscope insertion assembly according to claim 2 and wherein said coupling element comprises an optical window adapted for inspection by said optical assembly therethrough.

5. An endoscope insertion assembly according to claim 1 and wherein said pulling element is operative for detaching from said optical assembly following insertion of said optical assembly within said at least one lumen of said endoscope insertion tube.

6. An endoscope insertion assembly according to claim 5 and also comprising a coupling element operative for engaging said optical assembly with said endoscope insertion tube, and wherein said pulling element is detachably engaged with said coupling element for selectable detachment therefrom.

7. An endoscope insertion assembly according to claim 1 and also comprising a mechanical stopper operative to prevent said optical assembly from being pulled out and frontward of said endoscope insertion tube.

8. An endoscope insertion assembly according to claim 1 and wherein said endoscope insertion tube further comprises an instrument channel.

9. An endoscope insertion assembly according to claim 1 and wherein said endoscope insertion tube is a flexible endoscope insertion tube.

10. An endoscope insertion assembly according to claim 1 and wherein said endoscope insertion tube is generally fluid impermeable.

\* \* \* \* \*